US012708616B2

(12) United States Patent
Luu et al.

(10) Patent No.: US 12,708,616 B2
(45) Date of Patent: Aug. 18, 2026

(54) COMPOSITIONS AND METHODS OF TREATING AGE-RELATED RETINAL DYSFUNCTION

(71) Applicant: THE REGENTS OF THE UNIVERSITY OF CALIFORNIA, Oakland, CA (US)

(72) Inventors: Jennings Luu, Oakland, CA (US); Krzysztof Palczewski, Oakland, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 730 days.

(21) Appl. No.: 18/006,176

(22) PCT Filed: Jul. 21, 2021

(86) PCT No.: PCT/US2021/042634

§ 371 (c)(1), (2) Date: Jan. 20, 2023

(87) PCT Pub. No.: WO2022/020514

PCT Pub. Date: Jan. 27, 2022

(65) Prior Publication Data

US 2023/0372311 A1 Nov. 23, 2023

Related U.S. Application Data

(60) Provisional application No. 63/054,576, filed on Jul. 21, 2020.

(51) Int. Cl.

*A61K 31/437* (2006.01)
*A61K 31/506* (2006.01)
*A61P 27/02* (2006.01)

(52) U.S. Cl.

CPC .......... *A61K 31/437* (2013.01); *A61K 31/506* (2013.01); *A61P 27/02* (2018.01)

(58) Field of Classification Search

None

See application file for complete search history.

(56) References Cited

U.S. PATENT DOCUMENTS

| | | | | |
|---|---|---|---|---|
| 2008/0004311 | A1* | 1/2008 | Hellberg | A61K 31/192 514/408 |
| 2009/0253769 | A1* | 10/2009 | Filocamo | C12N 15/1137 435/6.12 |
| 2018/0291400 | A1* | 10/2018 | Zhang | C12N 5/10 |

FOREIGN PATENT DOCUMENTS

| | | | |
|---|---|---|---|
| WO | WO 2018/201146 | * 11/2018 | A61K 31/40 |

OTHER PUBLICATIONS

Wang et al (Nature Communications 9:1364, 2018) (Year: 2018).*
Hess-Stumpp et al (Int J Biochem & Cell Bio 39:1388-1405, 2007) (Year: 2007).*
Boumber et al (Expert Opin Investig Drugs 20:823-829, 2011) (Year: 2011).*
Ly et al (Optometry and Vision Science 94:246-259, 2016) (Year: 2016).*
Vougiouklakis et al (Oncotarget 9:31820-31831, 2018) (Year: 2018).*
Gong et al (PNAS 115:E3987-E3995, 2018) (Year: 2018).*
Nashine et al., Age-related macular degeneration (AMD) mitochondria modulate epigenetic mechanisms in retinal pigment epithelial cells, Experimental Eye Research, Jun. 19, 2019, vol. 189, p. 1-15.

* cited by examiner

*Primary Examiner* — Craig D Ricci
(74) *Attorney, Agent, or Firm* — Tarolli, Sundheim, Covell & Tummino LLP

(57) ABSTRACT

A method of treating and/or preventing age-related retinal dysfunction in a subject in need thereof includes administering to the subject a therapeutically effective amount of an agent that attenuates stress-induced chromatin remodeling associated with the age-related retinal dysfunction.

8 Claims, 14 Drawing Sheets

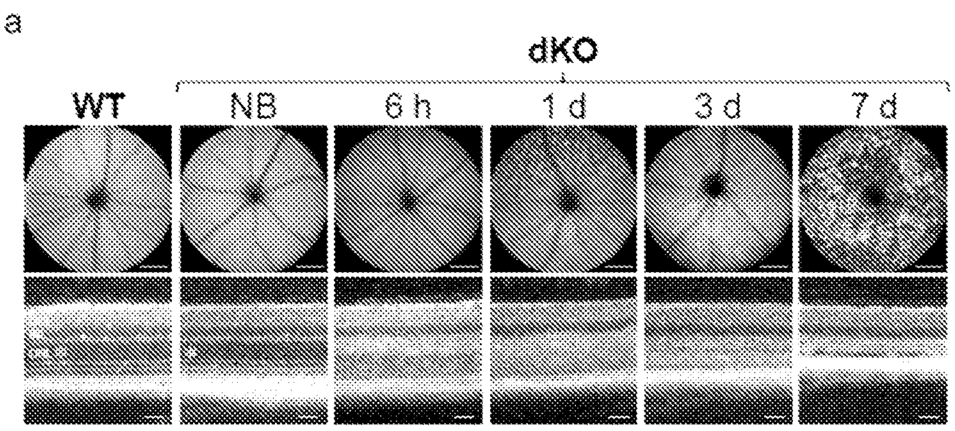
Fig. 3A
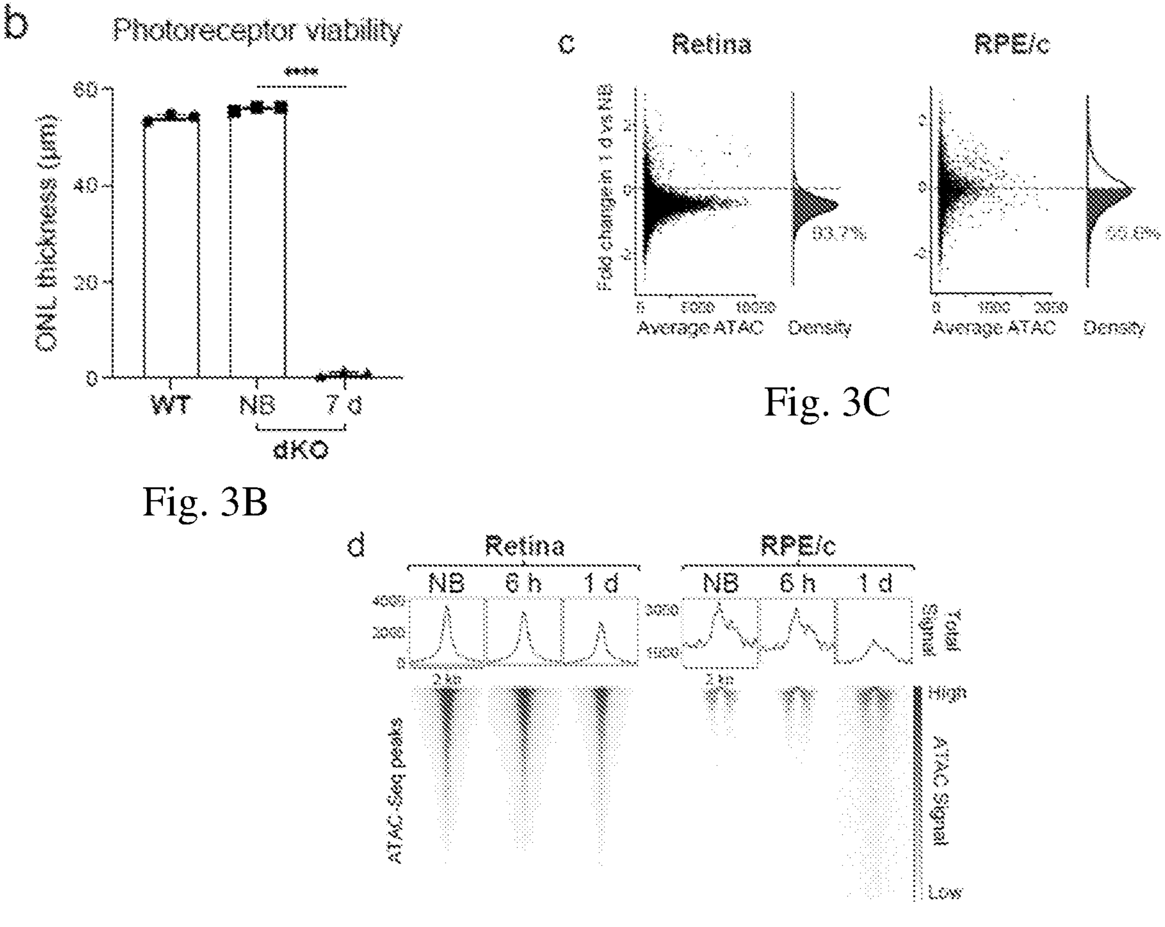
Fig. 3B
Fig. 3C
Fig. 3D

COMPOSITIONS AND METHODS OF TREATING AGE-RELATED RETINAL DYSFUNCTION

RELATED APPLICATION

This application claims priority from U.S. Provisional Application No. 63/054,576, filed Jul. 21, 2020, the subject matter of which is incorporated herein by reference in its entirety.

GOVERNMENT FUNDING

This invention was made with government support under grant EY009399 and EY027283, awarded by the National Institutes of Health. The government has certain rights in the invention.

BACKGROUND

In human aging and disease, a variety of genomic and epigenomic changes accumulate over a lifetime, resulting in deleterious effects to overall health. Aging is associated with increased transcriptional noise, in which key components of vital cellular signaling pathways are dysregulated as a result of the aberrant production and processing of gene transcripts. Unlike DNA mutations, epigenetic alterations are reversible, thereby providing avenues for the development of novel therapies to combat both transcriptional and translational dysregulation in age-associated diseases. These epigenetic changes include DNA methylation, histone modifications, and chromatin remodeling—all of which could ultimately be targeted therapeutically in efforts to normalize the transcriptome on a global level and improve organismal health.

To date, epigenetic modifications have been implicated in a variety of age-associated disorders, including cancer, cardiovascular disease, neurodegeneration, and visual dysfunction, such as age-related macular degeneration (AMD). Clinically, AMD is a leading cause of blindness in the elderly, characterized by progressive photoreceptor degeneration in the central retina. Up to 200 million individuals worldwide are affected by this disorder, yet no effective therapies currently exist for the most common (nonexudative or "dry") form of AMD.

SUMMARY

Embodiments described herein relate to compositions and methods of treating and/or preventing age-related retinal dysfunction and/or age-related visual impairment and, particularly, relates to compositions and methods of treating and/or preventing chronic retinal degenerative diseases, such as age-related macular degeneration (AMD).

Age-related retinal dysfunction includes chronic, multifactorial disorders characterized by progressive photoreceptor degeneration in the central retina. Disease progression involves epigenetic changes in chromatin accessibility resulting from environmental exposures and chronic stress. We found that a photosensitive mouse model of acute stress-induced photoreceptor degeneration recapitulates the epigenetic hallmarks of human age-related retinal dysfunction. Global epigenomic profiling was accomplished by employing an Assay for Transposase-Accessible Chromatin using Sequencing (ATAC-Seq), which revealed an association between decreased chromatin accessibility and stress-induced photoreceptor cell death. The epigenomic changes induced by light damage include reduced euchromatin and increased heterochromatin abundance, resulting in transcriptional and translational dysregulation that ultimately drives photoreceptor apoptosis and an inflammatory reactive gliosis in the retina. We further found that histone-modifying enzymes, such as histone deacetylase and/or histone methyltransferase, are involved in promoting reduced chromatin accessibility in age-related retinal dysfunction, and that inhibition of the histone-modifying enzymes, such as histone deacetylase and/or histone methyltransferase, can ameliorate light damage in the mouse model of acute stress-induced photoreceptor degeneration. This supports a causal link between decreased chromatin accessibility and photoreceptor degeneration, thereby elucidating a new therapeutic strategy to treat and/or prevent age-related retinal dysfunction.

Accordingly, a method of treating and/or preventing age-related retinal dysfunction in a subject in need thereof can include administering to the subject a therapeutically effective amount of an agent that attenuates stress-induced chromatin remodeling associated with the age-related retinal dysfunction and treats and/or prevents the age-related retinal dysfunction in the subject.

In some embodiments, the stress-induced chromatin remodeling includes a stress induced reduction in chromatin accessibility.

In some embodiments, the age-related retinal dysfunction is associated with an increase in histone deacetylase and/or histone methyltransferase in the subject's eye. For example, the age-related retinal dysfunction can be associated with an increase in histone deacetylase 11 (HDAC11) and/or suppressor of variegation 3-9 homolog 2 (SUV39H2) in the subject's eye.

In some embodiments, the age-related retinal dysfunction is associated with a decrease in H3K27ac in the retina and/or an increase in H3K9me in the retinal pigment epithelium and/or choroid of the subject, and the agent is administered to the subject at an amount effective to increase H3K27ac in the retina and/or decrease in H3K9me in the retinal pigment epithelium and/or choroid of the subject.

In some embodiments, the age-related retinal dysfunction can manifest as at least one of the following conditions: autofluorescent spots indicative of retinal pathology detected in the fundus by Scanning Laser Ophthalmoscopy (SLO), thinning of the photoreceptor containing outer nuclear layer (ONL) as characterized by Optical Coherence Tomography (OCT), a global reduction of chromatin accessibility as determined by an Assay for Transposase-Accessible Chromatin using Sequencing (ATAC-Seq), and photoreceptor degeneration.

In some embodiments, the agent can include an inhibitor of histone deacetylase and/or an inhibitor of histone methyltransferase, such as an inhibitor of HDAC11 and/or an inhibitor of SUV39H2.

In other embodiments, the agent can be a selective inhibitor of HDAC11 and/or a selective inhibitor of SUV39H2.

In some embodiments, the selective HDAC11 inhibitor can include at least one of SIS17, Quisinostat (JNJ-26481585), Fimepinostat (CUDC-907), Pracinostat (SB939), Mocetinostat (MGCD0103, MG0103), or Domatinostat (4SC-202).

In some embodiments, the selective SUV39H2 inhibitor can include at least one of OTS186935 or OTS193320.

In some embodiments, the agent is effective to inhibit bright light-induced retinal damage in a $Rdh8^{-/-}Abca4^{-/-}$ mouse.

In some embodiments, the agent can be delivered to the subject by at least one of topical administration, systemic administration, intravitreal injection, and intraocular delivery.

In other embodiments, the agent can be provided in an ocular preparation for sustained delivery.

In some embodiments, the age-related retinal dysfunction can be age-related macular degeneration (AMD), such as dry AMD or wet AMD.

Other embodiments relate to a method of treating and/or preventing stress-induced photoreceptor degeneration in a subject in need thereof by administering to the subject a therapeutically effective amount of an agent that attenuates stress induced reduction in chromatin accessibility in the subject's eye. The stress-induced photoreceptor degeneration can be associated an increase in histone deacetylase and/or histone methyltransferase in the subject's eye.

In some embodiments, the stress-induced photoreceptor degeneration is associated with a decrease in H3K27ac in the retina and/or an increase in H3K9me in the retinal pigment epithelium and/or choroid of the subject, and the agent is administered to the subject at an amount effective to increase H3K27ac in the retina and/or decrease in H3K9me in the retinal pigment epithelium and/or choroid of the subject.

In some embodiments, the stress-induced photoreceptor degeneration can manifest as at least one of the following conditions: autofluorescent spots indicative of retinal pathology detected in the fundus by Scanning Laser Ophthalmoscopy (SLO), thinning of the photoreceptor containing outer nuclear layer (ONL) as characterized by Optical Coherence Tomography (OCT), and a global reduction of chromatin accessibility as determined by an Assay for Transposase-Accessible Chromatin using Sequencing (ATAC-Seq).

In some embodiments, the agent can include an inhibitor of histone deacetylase and/or an inhibitor of histone methyltransferase, such as an inhibitor of HDAC11 and/or an inhibitor of SUV39H2.

In other embodiments, the agent can be a selective inhibitor of HDAC11 and/or a selective inhibitor of SUV39H2.

In some embodiments, the selective HDAC11 inhibitor can include at least one of SIS17, Quisinostat (JNJ-26481585), Fimepinostat (CUDC-907), Pracinostat (SB939), Mocetinostat (MGCD0103, MG0103), or Domatinostat (4SC-202).

In some embodiments, the selective SUV39H2 inhibitor can include at least one of OTS186935 or OTS193320.

DETAILED DESCRIPTION

Figure 1:
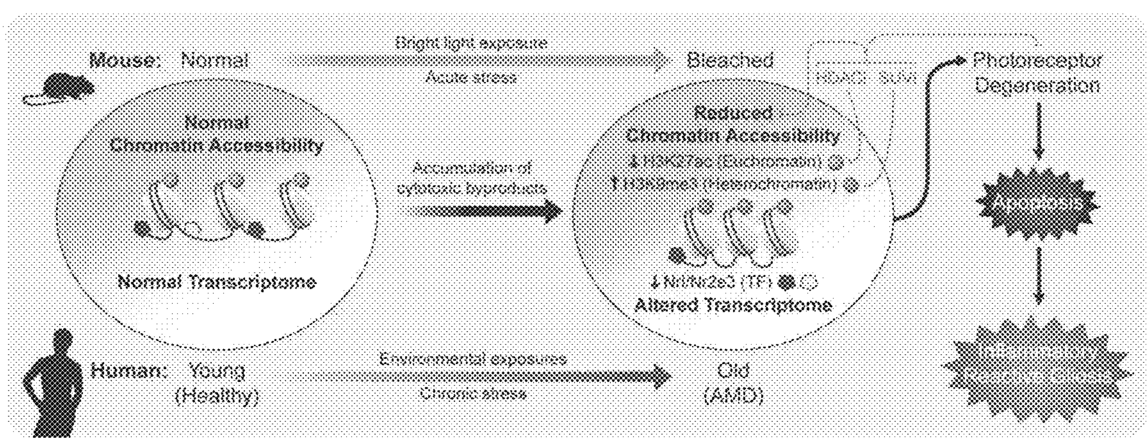
FIG. 1 illustrates a schematic showing pathogenesis of photoreceptor degeneration associated with decreased chromatin accessibility. In photosensitive dKO mice and humans that develop AMD, stress-induced cytotoxic byproduct accumulation drives global reduction in chromatin accessibility and downregulation of transcription factors (TF), resulting in an altered transcriptome that culminates in photoreceptor cell death and reactive inflammation. Administration of Mocetinostat, a pharmacological inhibitor of HDAC11 (HDACi), or OTS186935, a SUV39H2-selective inhibitor (SUVi), attenuates stress-induced chromatin remodeling, thereby ameliorating stress-induced photoreceptor degeneration and associated retinal pathology.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.,", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

As used herein, the term "age-related retinal dysfunction" refers to age-related decreases in retinal photoreceptor function. The term is meant to include the age-related impairments related to photoreceptor cell death, structural abnormalities, and retinal pathology that have been observed in both animal and human studies of aging. In one aspect, the age-related retinal dysfunction involves a stress-induced reduction in global chromatin accessibility. In another aspect, the age-related retinal dysfunction may manifest as age-related macular degeneration (AMD), which can occur in either wet or dry forms.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected. More specifically, the compounds and methods described herein which are used to treat a subject with age-related retinal dysfunction generally are provided in a therapeutically effective amount to achieve an improvement in age-related retinal dysfunction or an inhibited development of age-related retinal dysfunction in the visual system of an aging subject, as compared with a comparable visual system not receiving the drug. An improvement in age-related retinal dysfunction includes long-term (e.g., as measured in weeks or months) improvement or restoration of photoreceptor function in a visual system, as compared with a comparable visual system not receiving the drug. Improvement also includes stabilization of, or minimization of additional degradation in, a vertebrate visual system, as compared with a comparable vertebrate visual system not receiving the drug.

The terms "preventing," "prevention," and the like are used generally to mean preventing or inhibiting deterioration or further deterioration of the visual system of an aging subject, as compared with a comparable visual system not receiving the drug.

A "patient," "subject," or "host" to be treated by the subject compositions and methods described herein may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The terms "prophylactic" or "therapeutic" treatment is art-recognized and includes administration to the host of one or more of the subject compositions. If it is administered prior to clinical manifestation of the unwanted condition then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

By "reduces" or "increases" is meant a negative or positive alteration, respectively, of at least 10%, 25%, 50%, 75%, or 100%

The terms "agent", "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

The term "retina" refers to a region of the central nervous system with approximately 150 million neurons. It is located at the back of the eye where it rests upon a specialized epithelial tissue called retinal pigment epithelium or RPE. The retina initiates the first stage of visual processing by transducing visual stimuli in specialized neurons called "photoreceptors". Their synaptic outputs are processed by elaborate neural networks in the retina and then transmitted to the brain. The retina has evolved two specialized classes of photoreceptors to operate under a wide range of light conditions. "Rod" photoreceptors transduce visual images under low light conditions and mediate achromatic vision. "Cone" photoreceptors transduce visual images in dim to bright light conditions and mediate both color vision and high acuity vision.

Every photoreceptor is compartmentalized into two regions called the "outer" and "inner" segment. The inner segment is the neuronal cell body containing the cell nucleus. The inner segment survives for a lifetime in the absence of retinal disease. The outer segment is the region where the light sensitive visual pigment molecules are concentrated in a dense array of stacked membrane structures. Part of the outer segment is routinely shed and regrown in a diurnal process called outer segment renewal. Shed outer segments are ingested and metabolized by RPE cells.

The term "macula" refers to the central region of the retina, which contains the fovea where visual images are processed by long slender cones in high spatial detail ("visual acuity").

"Macular degeneration" is a form of retinal neurodegeneration, which attacks the macula and destroys high acuity vision in the center of the visual field. AMD can be in a "dry form" characterized by residual lysosomal granules called lipofuscin in RPE cells, and by extracellular deposits called "drusen". Drusen contain cellular waste products excreted by RPE cells. "Lipofuscin" and drusen can be detected clinically by ophthalmologists and quantified using fluorescence techniques. They can be the first clinical signs of macular degeneration.

Lipofuscin contains aggregations of A2E. Lipofuscin accumulates in RPE cells and poisons them by multiple known mechanisms. As RPE cells become poisoned, their biochemical activities decline and photoreceptors begin to degenerate. Extracellular drusen may further compromise RPE cells by interfering with their supply of vascular nutrients. Drusen also trigger inflammatory processes, which leads to choroidal neovascular invasions of the macula in one patient in ten who progresses to wet form AMD. Both the dry form and wet form progress to blindness.

The term "ERG" is an acronym for electroretinogram, which is the measurement of the electric field potential emitted by retinal neurons during their response to an experimentally defined light stimulus. ERG is a non-invasive measurement, which can be performed on either living subjects (human or animal) or a hemisected eye in solution that has been removed surgically from a living animal.

All percentages and ratios used herein, unless otherwise indicated, are by weight.

Embodiments described herein relate to compositions and methods of treating and/or preventing age-related retinal dysfunction and/or age-related visual impairment and, particularly, relates to compositions and methods of treating and/or preventing chronic retinal degenerative diseases, such as age-related macular degeneration (AMD).

Age-related retinal dysfunction includes chronic, multifactorial disorders characterized by progressive photoreceptor degeneration in the central retina. Disease progression involves epigenetic changes in chromatin accessibility resulting from environmental exposures and chronic stress. We found that a photosensitive mouse model of acute stress-induced photoreceptor degeneration recapitulates the epigenetic hallmarks of human age-related retinal dysfunction. Global epigenomic profiling was accomplished by employing an Assay for Transposase-Accessible Chromatin using Sequencing (ATAC-Seq), which revealed an association between decreased chromatin accessibility and stress-induced photoreceptor cell death. The epigenomic changes induced by light damage include reduced euchromatin and increased heterochromatin abundance, resulting in transcriptional and translational dysregulation that ultimately drives photoreceptor apoptosis and an inflammatory reactive gliosis in the retina. We further found that histone-modifying enzymes, such as histone deacetylase and/or histone methyltransferase, are involved in promoting reduced chromatin accessibility in age-related retinal dysfunction, and that inhibition of the histone-modifying enzymes, such as histone deacetylase and/or histone methyltransferase, can ameliorate light damage in the mouse model of acute stress-induced photoreceptor degeneration. This supports a causal link between decreased chromatin accessibility and photoreceptor degeneration, thereby elucidating a new therapeutic strategy to treat and/or prevent age-related retinal dysfunction.

In some embodiments, a method of treating and/or preventing age-related retinal dysfunction in a subject in need thereof can include administering to the subject a therapeutically effective amount of an agent that attenuates stress-induced chromatin remodeling associated with the age-related retinal dysfunction and treats and/or prevents the age-related retinal dysfunction in the subject. The stress-induced chromatin remodeling can include a stress induced reduction in chromatin accessibility.

In some embodiments, the age-related retinal dysfunction can be associated with an increase in histone deacetylase and/or histone methyltransferase in the subject's eye. For example, the age-related retinal dysfunction is associated with an increase in histone deacetylase 11 (HDAC11) and/or suppressor of variegation 3-9 homolog 2 (SUV39H2) in the subject's eye.

In some embodiments, the age-related retinal dysfunction is associated with a decrease in H3K27ac in the retina and/or an increase in H3K9me in the retinal pigment epithelium and/or choroid of the subject and the agent is administered to the subject at an amount effective to increase H3K27ac in the retina and/or decrease in H3K9me in the retinal pigment epithelium and/or choroid of the subject.

In some embodiments, the subject is an aging subject, such as a human, suffering from age-related retinal dysfunction. For example, an aging human subject is typically at least 45, or at least 50, or at least 60, or at least 65 years old. The subject can have an aging eye, which is characterized as having the age-related retinal dysfunction.

In some embodiments, the age-related retinal dysfunction may be manifested by one or more of the following conditions: autofluorescent spots indicative of retinal pathology detected in the fundus by Scanning Laser Ophthalmoscopy (SLO), thinning of the photoreceptor containing outer nuclear layer (ONL) as characterized by Optical Coherence Tomography (OCT), a global reduction of chromatin accessibility as determined by an Assay for Transposase-Accessible Chromatin using Sequencing (ATAC-Seq), and stress-induced photoreceptor degeneration modeling the pathogenesis of age-related macular degeneration (AMD).

In some embodiments, the age-related retinal dysfunction can include and/or be associated with, for example, retinal degeneration, macular degeneration, including age-related macular degeneration including the dry form and the wet form of age related macular degeneration, Stargardt's disease, Stargardt macular degeneration, fundus flavimaculatus, geographic atrophy, retinitis pigmentosa, ABCA4 mutation related retinal dystrophies, vitelliform (or Best) macular degeneration, adult onset form of vitelliform macular dystrophy, Sorsby's fundus dystrophy, Malattia leventinese (Doyne honeycomb or dominant radial drusen), diabetic retinopathy, diabetic maculopathy, diabetic macular edema, retinopathy that is or presents geographic atrophy and/or photoreceptor degeneration, retinopathy that is a lipofuscin-based retinal degeneration, aberrant modulation of lecithin-retinol acyltransferase in an eye, Leber's congenital amaurosis, retinal detachment, hemorrhagic retinopathy, hypertensive retinopathy, hereditary or non-hereditary optic neuropathy, inflammatory retinal disease, retinal blood vessel occlusion, retinopathy of prematurity, ischemia reperfusion related retinal injury, proliferative vitreoretinopathy, retinal dystrophy, uveitis, retinal disorders associated with Alzheimer's disease, retinal disorders associated with multiple sclerosis, retinal disorders associated with Parkinson's disease, retinal disorders associated with viral infection (cytomegalovirus or herpes simplex virus), retinal disorders related to light overexposure or myopia, retinal disorders associated with AIDS, glaucoma, genetic retinal dystrophies, traumatic injuries to the optic nerve, such as by physical injury, excessive light exposure, or laser light, neuropathies due to a toxic agent or caused by adverse drug reactions or vitamin deficiency, progressive retinal atrophy or degeneration, retinal diseases or disorders resulting from mechanical injury, chemical or drug-induced injury, thermal injury, radiation injury, light injury, or laser injury, hereditary and non-hereditary retinal dystrophy, ophthalmic injuries from environmental factors, such as light-induced oxidative retinal damage, laser-induced retinal damage, "flash bomb injury," or "light dazzle", refractive errors including but not limited to myopia, and retinal diseases related to A2E accumulation including RDS/PHRP2-related macular degeneration, Batten disease (juvenile neuronal ceroid lipofuscinosis), and central serous chorioretinopathy.

In some embodiments, the agent used to treat the age-related retinal dysfunction can include an inhibitor of histone deacetylase (HDAC) and/or an inhibitor of histone methyltransferase, such as an inhibitor of HDAC11 and/or an inhibitor of SUV39H2.

An inhibitor of HDAC can include any agent that inhibits expression and/or activity of an HDAC. Histone deacetylases (HDACs) are a group of hydrolases that remove the acetyl group from an ε-N-acetyl lysine amino acid of a histone or other substrate protein. Depending on sequence identity and domain organization, HDACs can be classified into class I (including HDAC1-3 and 8), class IIa (HDAC4, 5, 7, 9), class IIb (HDAC6 and 10), class III (including sirtuins) and class IV (HDAC11) (Dokmanovic et al, 2007, Mol Cancer Res October 5; 981-989).

The HDAC inhibitor can be a pan-HDAC inhibitor that inhibits the activity and/or expression of any class I (including HDAC1-3 and 8), class IIa (HDAC4, 5, 7, 9), class IIb (HDAC6 and 10), class III (including sirtuins) and/or class IV (HDAC11) HDAC or a selective HDAC inhibitor that inhibits the activity and/or expression of specific HDACs (e.g., HDAC11).

Examples of HDAC inhibitors according to the methods or compositions described herein include, without limitation, short-chain fatty acid (SCFA) derivatives, hydroxamic acids, cyclic peptides, aliphatic acids, depsipeptides and benzamides.

In some embodiments, the HDAC inhibitor is an SCFA derivative. Examples of SCFA inducing agents include propionic acid, butyric acid, succinic acid, valproic acid, fumaric acid monoethyl ester, dimethyl butyric acid, trifluorobutanol, chloropropionic acid, isopropionic acid, 2-oxypentanoic acid, 2,2- or 3,3-dimethyl butyric acid, 2,2- or 3,3-diethyl butyric acid, butyric acid ethyl ester, 2-methyl butanoic acid, fumaric acid, and amides and salts thereof. Other examples include methoxy acetic acid, methoxy propionic acid, N-acetylglycine, mercaptoacetic acid, 1- or 2-methyl cyclopropane carboxylic acid, squaric acid, 2- or 3-phenoxy propionic acid, methoxy butyric acid, phenoxy acetic acid, 2- or 3-phenoxy butyric acid, phenyl acetic acid, phenyl propionic acid, 3-phenyl butyric acid, ethyl-phenyl acetic acid, 4-chloro-2-phenoxy-2-propionic acid, n-dimethyl butyric acid glycine amide, o-benzoyl lactic acid, o-dimethyl butyric acid lactate, cinnamic acid, dihydrocinnamic acid ($C_6H_5CHCH_3COOH$), alpha-methyl-dihydrocinnamic acid, thiophenoxy acetic acid, and amines, amides, and salts of these chemicals. Useful amines and amides can include isobutylhydroxylamine, fumaric acid monoamide, fumaramide, succinamide, or isobutyramide.

In other embodiments, the HDAC inhibitor is a hydroxamic acid, such as Vorinostat/suberoyl anilide hydroxamic acid (SAHA), bishyroxamic acid/CBHA, Droxinostat, Quisinostat/JNJ-26481585, R306465/JNJ-16241199, CHR-3996, Belinostat/PXD101, Panobinostat/LBH-589, trichostatin A/TSA, ITF2357, m-carboxycinnamic acid, Givinostat/ITF2357, Pracinostat/SB939, Resminostat/4SC-201, Dacinostat/LAQ824, Abexinostat/PCI-24781, PCYC-0402, PCYC-0403, A161906, SB-55629, AR42, CUDC-101, Scriptaid, oxamflatin, and tubacin. In certain embodiments, the HDAC inhibitor is a pyrimidine hydroxamic acid, for example, JNJ-26481585, JNJ-16241199, or CHR-3996.

In other embodiments, the HDAC inhibitor is a hydroxamic acid derivative. In certain embodiments, the HDAC inhibitor is a pyrimidine hydroxamic acid. In some embodiments, the HDAC inhibitor is a non-piperidine-containing pyrimidine hydroxamic acid derivative. In certain embodiments, the HDAC inhibitor comprises an azabicyclo-hexane. In other embodiments, the HDAC inhibitor comprises fluorine. In certain embodiments, the HDAC inhibitor comprises a fluoroquinoline group.

In some embodiments, the HDAC inhibitor is a cyclic peptide. In certain embodiments, the cyclic peptide is HC-toxin, apcidin, Trapoxin A, Trapoxin B, WF-3161, chlamydocin, orazumamide A.

In some embodiments, the HDAC inhibitor is a depsipeptide. In certain embodiments, the depsipeptide is romidepsin (FK228), romidepsin analogs and derivatives, largazole, largazole analogs and derivatives, diheteropeptin, FR901375, or spiruchostatins.

In some embodiments, the HDAC inhibitor is a benzamide. In certain embodiments, the benzamide is Etinostat/MS275, RG-2833, CI994, 4SC-202, Mocetinostat/MGCD0103, RG2833, CDUC-101, or chidamide.

In some embodiments, the HDAC inhibitor is ACY-822, ACY-957, ACY-1071, ACY-1112, or ACY-1215.

In certain embodiments, the HDAC inhibitor used in the methods described herein inhibits HDAC11 expression and/or activity. For example, the HDAC11 inhibitor can specifically reduce or inhibit HDAC11's deacetylase activity and/or ability to associate with a protein complex. In other embodiments, an HDAC11 inhibitor can reduce expression of HDAC11. In some embodiments, agents that modulate (e.g., inhibit) HDAC11 are polynucleotides, polypeptides, peptides, peptide nucleic acids, antibodies and fragments thereof, small molecules, inorganic compounds and/or organic compounds. In some embodiments, agents that modulate (e.g., inhibit) HDAC11 include antagonists of HDAC11.

In some embodiments, HDAC11 inhibitors for use in accordance with the methods described herein are chemical compounds, including large or small inorganic or organic molecules.

In some embodiments, a small molecule HDAC11 inhibitor is at least 10-fold, 20-fold, 30-fold, 40-fold, 50-fold, 60-fold, 70-fold, 80-fold, 90-fold, 100-fold, 200-fold, 300-fold, 400-fold, 500-fold, 1,000-fold, 2,000-fold, 3,000-fold, or more selective for inhibition of HDAC11 over one, two, three, four, five, six, seven, eight, or more other histone deacetylase isoforms (e.g., HDAC1, HDAC2, HDAC3, HDAC4, HDAC5, HDAC6, HDAC7, HDAC8, HDAC9 and/or HDAC10). In certain embodiments, a HDAC11 inhibitor is at least 10-fold selective for HDAC11 over other histone deacetylase isoforms. In certain embodiments, the HDAC11 inhibitor is a small molecule that is at least 20-fold selective for HDAC11 over other histone deacetylase isoforms. In some embodiments, a small molecule HDAC11 inhibitor is at least 10-fold, 20-fold, 30-fold, 40-fold, 50-fold, 60-fold, 70-fold, 80-fold, 90-fold, 100-fold, 200-fold, 300-fold, 400-fold, 500-fold, 1,000-fold, 2,000-fold, 3,000-fold, or more selective for inhibition of HDAC11 each of HDAC1, HDAC2, HDAC3, HDAC4, HDAC5, HDAC6, HDAC7, HDAC8, HDAC9 and HDAC10.

In some embodiments, a small molecule inhibitor binds to HDAC11. In some embodiments, a small molecule binds to the catalytic domain of HDAC11 and interferes with or reduces its deacetylase activity or its ability to associate with other proteins to form a complex. In some embodiments, a small molecule HDAC11 inhibitor is at least 10-fold selective for the inhibition of HDAC11 over one or more other histone deacetylase isoforms (e.g., HDAC1, HDAC2, HDAC3, HDAC4, HDAC5, HDAC6, HDAC7, HDAC8, HDAC9 and/or HDAC10). In other embodiments, a small molecule inhibitor of HDAC11 is at least 200-fold selective for HDAC11 over other isoforms of histone deacetylases. In some embodiments, a small molecule HDAC11 inhibitor is at least 10-fold, 20-fold, 30-fold, 40-fold, 50-fold, 60-fold, 70-fold, 80-fold, 90-fold, 100-fold, 200-fold, 300-fold, 400-fold, 500-fold, 1,000-fold, 2,000-fold, 3,000-fold, or more selective for inhibition of HDAC11 over one or more other histone deacetylase isoforms (e.g., HDAC1, HDAC2, HDAC3, HDAC4, HDAC5, HDAC6, HDAC7, HDAC8, HDAC9 and/or HDAC10). In some embodiments, a small molecule HDAC11 inhibitor is at least 10-fold selective for the inhibition of HDAC11 over each of HDAC1, HDAC2, HDAC3, HDAC4, HDAC5, HDAC6, HDAC7, HDAC8, HDAC9 and HDAC10. In some embodiments, a HDAC11 inhibitor is specific for human HDAC11.

HDAC11 inhibitors or selective HDAC11 inhibitors, including small organic compounds, may be identified according to routine screening procedures available in the art, e.g., using commercially available libraries of such compounds. Exemplary small molecule HDAC11 inhibitors are described in further detail below.

In some embodiments, the HDAC11 inhibitor is selected from SIS17, Quisinostat (JNJ-26481585), Fimepinostat (CUDC-907), Pracinostat (SB939), Mocetinostat (MGCD0103, MG0103), or Domatinostat (4SC-202). SIS17 is a mammalian histone deacetylase 11 (HDAC 11)-specific inhibitor with IC50 of 0.83 μM. SIS17 inhibits the demyristoylation of HDAC11 substrate, serine hydroxymethyl transferase 2, without inhibiting other HDACs. Quisinostat (JNJ-26481585) 2HCl is a novel second-generation HDAC inhibitor with highest potency for HDAC1 with IC50 of 0.11 nM in a cell-free assay, modest potent to HDACs 2, 4, 10, and 11; greater than 30-fold selectivity against HDACs 3, 5, 8, and 9 and lowest potency to HDACs 6 and 7. Fimepinostat (CUDC-907) CUDC-907 is a dual PI3K and HDAC inhibitor for PI3Kα and HDAC1/2/3/11 with IC50 of 19 nM and 1.7 nM/5 nM/1.8 nM/2.8 nM, respectively. Pracinostat (SB939) is a potent pan-HDAC inhibitor with IC50 of 40-140 nM with exception for HDAC6. Mocetinostat (MGCD0103, MG0103) is a potent HDAC inhibitor with most potency for HDAC1 with IC50 of 0.15 μM in a cell-free assay, 2- to 10-fold selectivity against HDAC2, 3, and 11, and no activity to HDAC4, 5, 6, 7, and 8. Domatinostat (4SC-202) is a selective class I HDAC inhibitor with IC50 of 1.20 μM, 1.12 μM, and 0.57 μM for HDAC1, HDAC2, and HDAC3, respectively.

Still other examples of HDAC11 inhibitors and/or selective HDAC11 inhibitors are described in U.S. Pat. Nos. 6,541,661, 6,897,220, 6,953,783, 7,253,204, 7,282,608, 7,288,567, 7,595,343, 7,838,520, 7,868,204, 7,868,205, 8,030,344, 8,088,805, 8,093,264, 8,329,726, 8,338,437, 8,354,445, 8,399,452, 8,598,168, 8,673,911, 8,759,400, 8,796,330, 9,096,565, and 9,193,749, all of which are incorporated by reference in their entirety.

For example, HDAC11 inhibitors described in the above-noted U.S. patents can include a compound represented by the following formula or a pharmaceutically acceptable salt thereof:

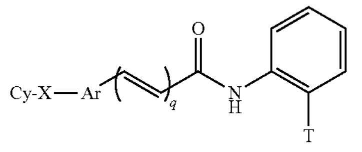

wherein;

X is selected from the group consisting of a chemical bond, L, W-L, L-W, L-W-L, and L-W'-L-W', Cy is aryl, heteroaryl, cycloalkyl or heterocyclyl, each of which is optionally substituted and each of which is optionally fused to one or more aryl or heteroaryl rings, or to one or more saturated or partially unsaturated cycloalkyl or heterocyclic rings, each of which rings is optionally substituted;

W, at each occurrence, is S, O, C═O, —NH—C(═O)—NH—, —$NHSO_2$—, or N($R^9$), where $R^9$ is selected from the group consisting of hydrogen, alkyl, hydroxyalkyl, and t-butoxycarbonyl;

W' at each occurrence is independently a chemical bond, S, O, or NH; and;

L, at each occurrence, is independently a chemical bond or $C_1$-$C_4$ alkylene; or Ar is arylene or heteroarylene, each of which is optionally substituted;

q is 0 or 1; and

T is $NH_2$ or OH;

provided that when Cy is naphthyl, X is —CH=2-, Ar is phenyl, and q is 0 or 1, T is not OH; and all of which are optionally substituted with one or more halogen. One example, of a compound having this formula is Mocetinostat (MGCD0103, MG0103).

In some embodiments, an inhibitor of histone methylation by protein methyltransferase (or histone methyltransferase inhibitor) can include any agent that inhibits expression and/or activity of a protein methyltransferase that promotes histone methylation. Histone methyltransferases (HMTs) are a class of enzymes that mediate the methylation of lysine or arginine residues of histones. So far, more than 50 lysine human methyltransferases (KMTs) have been reported. These enzymes have high selectivity for the histone lysine residue they target and are classified into two types: lysine methyltransferases (KMTs) and arginine methyltransferases (PRMTs). Based on catalytic domain sequence, KMTs are further divided into two families SET domain-containing KMTs, which include Su(var)3-9, Enhancer of Zeste (EZH), Trithorax, and non-SET domain-containing KMTs, such as the DOT1-like proteins. The structure of SET methyltransferase contains a SET domain, a pre-SET, and a post-SET domain. SET methyltransferases are further sub-divided into different families. The SET1 family bears the SET domain usually followed by a post-SET domain Two well-known methyltransferases, EZH1, and EZH2, belong to this family although they do not have the post-SET domain. The SET domain in the SET2 family is always flanked by a post-SET and an AWS domain, where the nuclear receptor binds to the SET domain, which contains proteins such as NSD1-3, the SETD2 and the SMYD family proteins. Members of the SUV39 family all demonstrate a pre-SET domain that includes SUV39H1, SUV39H2, G9a, GLP, ESET, and CLLL8.

In some embodiments, the histone methyltransferase inhibitor can be an inhibitor of H3K9 methyltransferase. Methylation of H3K9 in humans is controlled by PKMTs: SUV39H1 (suppressor of variegation 3-9 homologue 1), SUV39H2, G9a (euchromatic histone-lysine N-methyltransferase 2 (EHMT2)), GLP (G9a-like protein 1, also known as EHMT1), and SETDB1 (SET domain, bifurcated 1).

The inhibitor of H3K9 methyltransferase can be a pan-H3K9 methyl transferase inhibitor that inhibits the activity and/or expression of any H3K9 methyltransferase or a selective inhibitor of H3K9 methyltransferase that inhibits the activity and/or expression of specific H3K9 methyltransferases.

Examples of H3K9 methyltransferase inhibitors include chaetocin, BIX-01338, which contains a 2-(N-acyl)-aminobenzimidazole core, BIX-01294, which is a 2,4-diamino-6,7-dimethoxyquinazoline, UNC0224, UNC0321, BRD4770, BRD9539, and A-366. These compounds and other selective inhibitors of protein methyltransferases are disclosed in Kaniskan et al. *J. Med. Chem.* 2015, 58, 4, 1596-1629, which is incorporated by reference in its entirety.

In certain embodiments, H3K9 methyltransferase inhibitors used in the methods described herein can inhibit SUV39H2 expression and/or activity. For example, such SUV39H2 inhibitor specifically reduces or inhibits SUV39H2's H3K9 methyltransferase activity. In other embodiments, an SUV39H2 inhibitor can reduce expression of SUV39H2. In some embodiments, agents that modulate (e.g. inhibit) SUV39H2 are polynucleotides, polypeptides, peptides, peptide nucleic acids, antibodies and fragments thereof, small molecules, inorganic compounds and/or organic compounds. In some embodiments, agents that modulate (e.g., inhibit) SUV39H2 include antagonists of SUV39H2.

In some embodiments, SUV39H2 inhibitors for use in accordance with the methods described herein are chemical compounds, including large or small inorganic or organic molecules.

Examples of selective SUV39H2 inhibitors include OTS186935 ((S)-1-(2-(5-chloro-2,4-dimethoxyphenyl)imidazo[1,2-a]pyridin-7-yl)-N-(pyridin-4-ylmethyl)pyrrolidin-3-amine), OTS193320, and bicyclic analogues thereof that are disclosed in U.S. Patent Publication No. 2018/0273529, which is incorporated herein by reference in its entirety.

For example, bicyclic compounds disclosed in U.S. Patent Publication No. 2018/0273529 can include a compound represented by the following formula or a pharmaceutically acceptable salt thereof:

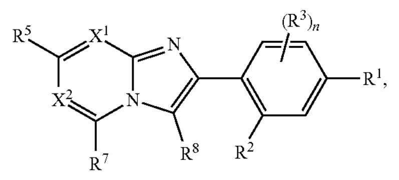

wherein, $R^1$ is selected from the group consisting of a halogen atom, hydroxy, $C_1$-$C_6$ alkyl, and $C_1$-$C_6$ alkoxy, wherein the alkyl and the alkoxy may be substituted with one or more substituents selected from $A^1$;

$R^2$ is selected from the group consisting of a hydrogen atom, a halogen atom, hydroxy, $C_1$-$C_6$ alkyl, $C_1$-$C_6$ alkoxy, and $C_3$-$C_{10}$ cycloalkoxy, wherein the alkyl and the alkoxy may be substituted with one or more substituents selected from $A^2$;

$R^3$ is independently selected from the group consisting of a halogen atom, cyano, nitro, hydroxy, carboxy, $C_1$-$C_6$ alkyl, $C_1$-$C_6$ alkoxy, ($C_1$-$C_6$ alkoxy)carbonyl, $C_1$-$C_6$ alkylthio, $C_1$-$C_6$ alkylsulfinyl, and $C_1$-$C_6$ alkylsulfonyl;

n is an integer selected from 0 to 3;

$X^1$ is N, or $CR^4$;

$X^2$ is N, or $CR^6$;

$R^4$ is selected from the group consisting of a hydrogen atom, a halogen atom, $C_1$-$C_6$ alkyl, and $C_1$-$C_6$ alkoxy;

$R^5$ and $R^6$ are independently selected from the group consisting of a hydrogen atom, a halogen atom, and Y, wherein at least one of $R^5$ and $R^6$ is Y;

Y is independently selected from the group consisting of hydroxy, $C_1$-$C_6$ alkyl optionally substituted with one or more substituents selected from $A^3$, $C_1$-$C_6$ alkoxy optionally substituted with one or more substituents selected from $A^3$, $—NR^{11}R^{12}$, $—CONR^{13}R^{14}$, $C_3$-$C_{10}$ cycloalkyl optionally substituted with one or more substituents selected from Rc, $C_6$-$C_{10}$ aryl optionally substituted with one or more substituents selected from Rd, 3- to 12-membered non-aromatic heterocyclyl optionally substituted with one or more substituents selected from Re, 5- to 10-membered heteroaryl optionally substituted with one or more substituents selected from Rf, and $—OR^{15}$;

$R^{11}$ is selected from the group consisting of a hydrogen atom, $C_1$-$C_6$ alkyl optionally substituted with one or more substituents selected from Ra, $C_3$-$C_{10}$ cycloalkyl optionally substituted with one or more substituents selected from Rb, $C_6$-$C_{10}$ aryl optionally substituted with one or more substituents selected from Rb, 5- to 10-membered heteroaryl optionally substituted with one or more substituents selected from Rb, 3- to 12-membered non-aromatic heterocyclyl optionally substituted with one or more substituents selected from Rb, ($C_1$-$C_6$ alkoxy)carbonyl optionally substituted with one or more substituents selected from Ra, ($C_1$-$C_6$ alkyl)carbonyl optionally substituted with one or more substituents selected from Ra, ($C_3$-$C_{10}$ cycloalkyl)carbonyl optionally substituted with one or more substituents selected from Rg, ($C_6$-$C_{10}$ aryl)carbonyl optionally substituted with one or more substituents selected from Rh, (3- to 12-membered non-aromatic heterocyclyl) carbonyl optionally substituted with one or more substituents selected from Rg, (5- to 10-membered heteroaryl)carbonyl optionally substituted with one or more substituents selected from Rg, aminocarbonyl, ($C_1$-$C_6$ alkyl)aminocarbonyl, and di($C_1$-$C_6$ alkyl)aminocarbonyl;

$R^{12}$ is selected from the group consisting of a hydrogen atom, and $C_1$-$C_6$ alkyl optionally substituted with one or more substituents selected from Ra;

$R^{13}$ is selected from the group consisting of a hydrogen atom, $C_1$-$C_6$ alkyl optionally substituted with one or more substituents selected from Ra, $C_3$-$C_{10}$ cycloalkyl optionally substituted with one or more substituents selected from Rg, $C_6$-$C_{10}$ aryl optionally substituted with one or more substituents selected from Rh, 5- to 10-membered heteroaryl optionally substituted with one or more substituents selected from Rg, and 3- to 12-membered non-aromatic heterocyclyl optionally substituted with one or more substituents selected from Rg;

$R^{14}$ is selected from the group consisting of a hydrogen atom, and $C_1$-$C_6$ alkyl optionally substituted with one or more substituents selected from Ra;

$R^{15}$ is selected from the group consisting of $C_3$-$C_{10}$ cycloalkyl optionally substituted with one or more substituents selected from Rc, $C_6$-$C_{10}$ aryl optionally substituted with one or more substituents selected from Rd, 4- to 12-membered heterocyclyl optionally substituted with one or more substituents selected from Re, and 5- to 10-membered heteroaryl optionally substituted with one or more substituents selected from Rf;

$A^1$ is independently selected from the group consisting of a halogen atom and cyano;

$A^2$ is independently selected from the group consisting of a halogen atom, cyano, amino, $C_1$-$C_6$ alkylamino, di($C_1$-$C_6$ alkyl)amino, $C_1$-$C_6$ alkylthio, $C_1$-$C_6$ alkylsulfinyl, $C_1$-$C_6$ alkylsulfonyl $C_3$-$C_{10}$ cycloalkyl, and $C_1$-$C_6$ alkoxy;

$A^3$ independently is selected from the group consisting of a halogen atom, cyano, amino, $C_1$-$C_6$ alkylamino, di($C_1$-$C_6$ alkyl)amino, $C_1$-$C_6$ alkylthio, $C_1$-$C_6$ alkylsulfinyl, $C_1$-$C_6$ alkylsulfonyl, $C_3$-$C_{10}$ cycloalkylsulfonyl, $C_3$-$C_{10}$ cycloalkyl, and $C_1$-$C_6$ alkoxy;

Ra is independently selected from the group consisting of a halogen atom, hydroxy, $C_1$-$C_6$ alkoxy, cyano, ($C_1$-$C_6$ alkoxy)carbonyl, carboxy, ($C_1$-$C_6$ alkoxy)carbonylamino, ($C_1$-$C_6$ alkyl)carbonylamino, amino, $C_1$-$C_6$ alkylamino, di($C_1$-$C_6$ alkyl)amino, aminocarbonyl, ($C_1$-$C_6$ alkyl)aminocarbonyl, di($C_1$-$C_6$ alkyl)aminocarbonyl, $C_1$-$C_6$ alkylsulfonylamino, $C_3$-$C_{10}$ cycloalkylsulfonylamino, di($C_1$-$C_6$ alkyl)phosphono, $C_7$-$C_{14}$ aralkyl, $C_3$-$C_{10}$ cycloalkyl optionally substituted with one or more substituents selected from Rg, $C_6$-$C_{10}$ aryl optionally substituted with one or more substituents selected from Rh, 5- to 10-membered heteroaryl optionally substituted with one or more substituents selected from Rg, and 4- to 12-membered non-aromatic heterocyclyl optionally substituted with one or more substituents selected from Rg;

Rb is independently selected from the group consisting of a halogen atom, hydroxy, $C_1$-$C_6$ alkyl optionally substituted with one or more substitutents selected from Ra, $C_1$-$C_6$ alkoxy optionally substituted with one or more substitutents selected from Ra, cyano, ($C_1$-$C_6$ alkoxy)carbonyl, carboxy, $—NR^{21}R^{22}$, $—CONR^{13}R^{24}$, di($C_1$-$C_6$ alkyl)phosphono, $C_3$-$C_{10}$ cycloalkyl optionally substituted with one or more substituents selected from Rg, $C_6$-$C_{10}$ aryl optionally substituted with one or more substituents selected from Rh, 5- to 10-membered heteroaryl optionally substituted with one or more substituents selected from Rg, and 3- to 12-membered non-aromatic heterocyclyl optionally substituted with one or more substituents selected from Rg;

Rc, Re and Rf are independently selected from the group consisting of a halogen atom, hydroxy, cyano, carboxy, $—NR^{21}R^{22}$, $—CONR^{23}R^{24}$, $—N{=}CH—R^{25}$, $C_1$-$C_6$ alkyl optionally substituted with one or more substituents selected from Ra, ($C_1$-$C_6$ alkoxy) $C_1$-$C_6$ alkyl optionally substituted with one or more substituents selected from Ra, ($C_1$-$C_6$ alkyl)carbonyl optionally substituted with one or more substituents selected from Ra, ($C_1$-$C_6$ alkoxy)carbonyl, ($C_6$-$C_{10}$ aryl)carbonyl optionally substituted with one or more substituents selected from Rh, ($C_3$-$C_{10}$ cycloalkyl)carbonyl optionally substituted with one or more substituents selected from Rg, (3- to 12-membered non-aromatic heterocyclyl)carbonyl optionally substituted with one or more substituents selected from Rg, $C_3$-$C_{10}$ cycloalkyl optionally substituted with one or more substituents selected from Rg, 3- to 12-membered non-aromatic heterocyclyl optionally substituted with one or more substituents selected from Rg, aminocarbonyl, ($C_1$-$C_6$ alkyl)aminocarbonyl optionally substituted with one or more substituents selected from Ra, di($C_1$-$C_6$ alkyl) aminocarbonyl optionally substituted with one or more substituents selected from Ra, [($C_1$-$C_6$ alkyl)aminocarbonyl] $C_1$-$C_6$ alkyl optionally substituted with one or more substituents selected from Ra, [di($C_1$-$C_6$ alkyl) aminocarbonyl]$C_1$-$C_6$ alkyl optionally substituted with one or more substituents selected from Ra, 5- to 10-membered heteroaryl optionally substituted with one or more substituents selected from Rg, $C_1$-$C_6$ alkylsulfonyl optionally substituted with one or more halogen atoms, $C_3$-$C_{10}$ cycloalkylsulfonyl optionally substituted with one or more substituents selected from Rg, ($C_6$-$C_{10}$ aryl)sulfonyl optionally substituted with one or more substituents selected from Rh, $C_7$-$C_{14}$ aralkylsulfonyl, (3- to 12-membered non-aromatic heterocyclyl)sulfonyl optionally substituted with one or more substituents selected from Rg, 5- to 10-membered heteroarylcarbonyl optionally substituted with one or more substituents selected from Rg, 5- to 10-membered heteroarylsulfonyl optionally substituted with one or more substituents selected from Rg, aminosulfonyl, $C_1$-$C_6$ alkylaminosulfonyl, di($C_1$-$C_6$ alkyl)aminosulfonyl, di($C_1$-$C_6$alkyl)phosphono, and oxo;

Rd is independently selected from the group consisting of a halogen atom, hydroxy, cyano, carboxy, —$NR^{21}R^{22}$, —$CONR^{23}R^{24}$, $C_1$-$C_6$ alkyl optionally substituted with one or more substituents selected from Ra, ($C_1$-$C_6$ alkoxy) $C_1$-$C_6$ alkyl optionally substituted with one or more substituents selected from Ra, ($C_1$-$C_6$ alkyl)carbonyl optionally substituted with one or more substituents selected from Ra, ($C_1$-$C_6$ alkoxy)carbonyl, ($C_6$-$C_{10}$ aryl)carbonyl optionally substituted with one or more substituents selected from Rh, ($C_3$-$C_{10}$ cycloalkyl)carbonyl optionally substituted with one or more substituents selected from Rg, (3- to 12-membered non-aromatic heterocyclyl)carbonyl optionally substituted with one or more substituents selected from Rg, $C_3$-$C_{10}$ cycloalkyl optionally substituted with one or more substituents selected from Rg, 3- to 12-membered non-aromatic heterocyclyl optionally substituted with one or more substituents selected from Rg, aminocarbonyl, ($C_1$-$C_6$ alkyl)aminocarbonyl optionally substituted with one or more substituents selected from Ra, di($C_1$-$C_6$ alkyl)aminocarbonyl optionally substituted with one or more substituents selected from Ra, [($C_1$-$C_6$ alkyl)aminocarbonyl] $C_1$-$C_6$ alkyl optionally substituted with one or more substituents selected from Ra, [di($C_1$-$C_6$ alkyl)aminocarbonyl] $C_1$-$C_6$ alkyl optionally substituted with one or more substituents selected from Ra, 5- to 10-membered heteroaryl optionally substituted with one or more substituents selected from Rg, $C_1$-$C_6$ alkylsulfonyl optionally substituted with one or more halogen atoms, $C_3$-$C_{10}$ cycloalkylsulfonyl optionally substituted with one or more substituents selected from Rg, ($C_6$-$C_{10}$ aryl)sulfonyl optionally substituted with one or more substituents selected from Rh, $C_7$-$C_{14}$ aralkylsulfonyl, (3- to 12-membered non-aromatic heterocyclyl)sulfonyl optionally substituted with one or more substituents selected from Rg, 5- to 10-membered heteroarylsulfonyl optionally substituted with one or more substituents selected from Rg, aminosulfonyl, $C_1$-$C_6$ alkylaminosulfonyl, di($C_1$-$C_6$ alkyl)aminosulfonyl, and di($C_1$-$C_6$ alkyl)phosphono;

Rg is independently selected from the group consisting of nitro, hydroxy, $C_1$-$C_6$ alkyl optionally substituted with one or more halogen atoms, $C_1$-$C_6$ alkoxy optionally substituted with one or more halogen atoms, a halogen atom, amino, cyano, $C_1$-$C_6$ alkylamino optionally substituted with one or more hydroxy groups, di($C_1$-$C_6$ alkyl)amino optionally substituted with one or more hydroxy groups, $C_3$-$C_{10}$ cycloalkylamino, ($C_1$-$C_6$ alkyl)carbonyl, ($C_1$-$C_6$ alkoxy)carbonyl, $C_1$-$C_6$ alkylsulfonyl, $C_3$-$C_{10}$ cycloalkylsulfonyl, $C_7$-$C_{14}$ aralkyl optionally substituted with one or more substituents selected from Ri, $C_6$-$C_{10}$ aryl optionally substituted with one or more substituents selected from Ri, $C_3$-$C_{10}$ cycloalkyl optionally substituted with one or more substituents selected from Ri, 3- to 12-membered non-aromatic heterocyclyl optionally substituted with one or more substituents selected from Ri, 5- to 10-membered heteroaryl optionally substituted with one or more substituents selected from Ri, and oxo;

Rh is independently selected from the group consisting of nitro, hydroxy, $C_1$-$C_6$ alkyl optionally substituted with one or more halogen atoms, $C_1$-$C_6$ alkoxy optionally substituted with one or more halogen atoms, a halogen atom, amino, cyano, $C_1$-$C_6$ alkylamino, di($C_1$-$C_6$ alkyl) amino, $C_1$-$C_6$ alkylcarbonyl, ($C_1$-$C_6$ alkoxy)carbonyl, ($C_1$-$C_6$ alkoxy)carbonylamino, N—($C_1$-$C_6$ alkoxy)carbonyl-N—($C_1$-$C_6$ alkyl)amino, $C_1$-$C_6$ alkylsulfonyl, $C_3$-$C_8$ cycloalkylsulfonyl, $C_7$-$C_{14}$ aralkyl optionally substituted with one or more substituents selected from Ri, $C_6$-$C_{10}$ aryl optionally substituted with one or more substituents selected from Ri, $C_3$-$C_8$ cycloalkyl optionally substituted with one or more substituents selected from Ri, 3- to 12-membered non-aromatic heterocyclyl optionally substituted with one or more substituents selected from Ri, and 5- to 10-membered heteroaryl optionally substituted with one or more substituents selected from Ri;

Ri is independently selected from the group consisting of nitro, hydroxy, $C_1$-$C_6$ alkyl optionally substituted with one or more substituents selected from a halogen atom and hydroxy, a halogen atom, amino, cyano, $C_1$-$C_6$ alkylamino, di($C_1$-$C_6$ alkyl)amino, $C_1$-$C_6$ alkylcarbonyl optionally substituted with one or more substituents selected from phenyl and hydroxy, ($C_1$-$C_6$ alkoxy) carbonyl optionally substituted with one or more substituents selected from phenyl and hydroxy, $C_1$-$C_6$ alkylsulfonyl, $C_3$-$C_8$ cycloalkylsulfonyl, $C_1$-$C_6$ alkylsulfonylamino, $C_3$-$C_8$ cycloalkylsulfonylamino, and oxo;

$R^{21}$ is selected from the group consisting of a hydrogen atom, $C_1$-$C_6$ alkyl optionally substituted with one or more substituents selected from Ra, $C_6$-$C_{10}$ aryl optionally substituted with one or more substituents selected from Rh, 4- to 12-membered heterocyclyl optionally substituted with one or more substituents selected from Rg, 5- to 10-membered heteroaryl optionally substituted with one or more substituents selected from Rg, ($C_1$-$C_6$ alkoxy)carbonyl optionally substituted with one or more substituents selected from Ra, ($C_1$-$C_6$ alkyl) carbonyl optionally substituted with one or more substituents selected from Ra, ($C_3$-$C_{10}$ cycloalkyl)carbonyl, ($C_6$-$C_{10}$ aryl)carbonyl optionally substituted with one or more substituents selected from Rh, (3- to 12-membered non-aromatic heterocyclyl)carbonyl optionally substituted with one or more substituents selected from Rg, (5- to 10-membered heteroaryl) carbonyl optionally substituted with one or more substituents selected from Rg, aminocarbonyl, ($C_1$-$C_6$ alkyl)aminocarbonyl optionally substituted with one or more substituents selected from Ra, di($C_1$-$C_6$ alkyl) aminocarbonyl optionally substituted with one or more substituents selected from Ra, $C_1$-$C_6$ alkylsulfonyl optionally substituted with one or more halogen atoms, $C_7$-$C_{14}$ aralkylsulfonyl, $C_3$-$C_{10}$ cycloalkylsulfonyl, aminosulfonyl, $C_1$-$C_6$ alkylaminosulfonyl, di($C_1$-$C_6$ alkyl)aminosulfonyl, and di($C_1$-$C_6$ alkyl)phosphono;

$R^{22}$ is selected from the group consisting of a hydrogen atom, and $C_1$-$C_6$ alkyl optionally substituted with one or more substituents selected from Ra;

$R^{23}$ is selected from the group consisting of a hydrogen atom, $C_1$-$C_6$ alkyl optionally substituted with one or more substituents selected from Ra, [($C_1$-$C_6$ alkyl) amino] $C_1$-$C_6$ alkyl optionally substituted with one or more substituents selected from Ra, [di($C_1$-$C_6$ alkyl) amino] $C_1$-$C_6$ alkyl optionally substituted with one or more substituents selected from Ra, $C_3$-$C_{10}$ cycloalkyl optionally substituted with one or more substituents selected from Rg, $C_6$-$C_{10}$ aryl optionally substituted with one or more substituents selected from Rh, 5- to 10-membered heteroaryl optionally substituted with one or more substituents selected from Rg, and 3- to 12-membered non-aromatic heterocyclyl optionally substituted with one or more substituents selected from Rg;

$R^{24}$ is selected from the group consisting of a hydrogen atom, and $C_1$-$C_6$ alkyl optionally substituted with one or more substituents selected from Ra;

$R^{25}$ is selected from the group consisting of $C_1$-$C_6$ alkyl optionally substituted with one or more substituents selected from Ra, $C_3$-$C_{10}$ cycloalkyl optionally substituted with one or more substituents selected from Re, $C_6$-$C_{10}$ aryl optionally substituted with one or more substituents selected from Rd, 4- to 12-membered heterocyclyl optionally substituted with one or more substituents selected from Re, and 5- to 10-membered heteroaryl optionally substituted with one or more substituents selected from Rf;

$R^7$ is selected from the group consisting of a hydrogen atom, a halogen atom, $C_1$-$C_6$ alkyl, and $C_1$-$C_6$ alkoxy;

$R^8$ is selected from the group consisting of a hydrogen atom, a halogen atom, $C_1$-$C_6$ alkyl, and $C_1$-$C_6$ alkoxy; and wherein a sulfur atom included in heterocyclyl or heteroaryl may be oxidized to be SO or $SO_2$.

It will be appreciated that the HDAC11 inhibitor and/or SUV39H2 inhibitor used in the methods described herein need not be limited to small molecules and that any HDAC11 inhibitor and/or SUV39H2 inhibitor known in the art may be used. Such other HDAC11 inhibitors and/or SUV39H2 inhibitors can include dominant negative inhibitors of HDAC11 and/or SUV39H2 which reduce or block the activity of wild type HDAC11 and/or SUV39H2, various polynucleotides for use as inhibitors of HDAC11 and/or SUV39H2 expression and/or activity, such as antisense RNA, RNA interference (RNAi) reagents, or short-interfering RNAs (siRNA), designed to specifically inhibit expression of HDAC11 and/or SUV39H2, CRISPR gene editing system used to silence, enhance or mutate the HDAC11 gene and/or SUV39H2 gene, and antibody agents that specifically bind HDAC11 and/or SUV39H2.

In some embodiments, the HDAC11 inhibitors and/or SUV39H2 inhibitors that can inhibit retinal degeneration upon administration to a subject can be selected using an in vivo assays that measure the ability of a the HDAC11 inhibitors and/or SUV39H2 inhibitors to respectively rescue the stress-induced reduction in euchromatin abundance observed in the retina of photobleached dKO $Rdh8^{-/-}$ $Abca4^{-/-}$ mice and attenuate the stress-induced increase in heterochromatin abundance observed in the RPE/choroid of bleached dKO $Rdh8^{-/-}Abca4^{-/-}$ mice.

In some embodiments, the HDAC11 inhibitors and/or SUV39H2 inhibitors when administered to a $Rdh8^{-/-}$ $Abca4^{-/-}$ mouse increase the optical coherence tomography OCT score of the mouse in comparison to untreated control animal. Additionally, in some embodiments, therapeutic efficacy of the HDAC11 inhibitors and/or SUV39H2 inhibitors can be determined using an in vitro assay that measures the ability of the HDAC11 inhibitors and/or SUV39H2 inhibitors to improve viability of photoreceptor or RPE cells treated with the HDAC11 inhibitors and/or SUV39H2 inhibitors.

The HDAC11 inhibitors and/or SUV39H2 inhibitors used in methods described herein to treat age-related retinal dysfunction can be administered to the subject using standard delivery methods including, for example, topical and systemic delivery methods, such as ophthalmic, parenteral, subcutaneous, intravenous, intraarticular, intrathecal, intramuscular, intraperitoneal, intradermal injections, or by intravitreal injection, subretinal injection, intraocular injection or periocular injection.

Formulation of the pharmaceutical compositions comprising the HDAC11 inhibitors and/or SUV39H2 inhibitors for use in the modes of administration noted above (and others) are known in the art and are described, for example, in Remington's Pharmaceutical Sciences (18th edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y., U.S.A., 2005; and Mathiowitz et al., eds., Bioadhesive Drug Delivery Systems, Drugs and the Pharmaceutical Sciences Series, Marcel Dekker, Inc., N.Y., U.S.A., 1999. HDAC11 inhibitors and/or SUV39H2 inhibitors can be formulated into pharmaceutical compositions containing pharmaceutically acceptable non-toxic excipients and carriers. The excipients are all components present in the pharmaceutical formulation other than the active ingredient or ingredients. Suitable excipients and carriers can be composed of materials that are considered safe and effective and may be administered to an individual without causing undesirable biological side effects, or unwanted interactions with other medications. Suitable excipients and carriers are those, which are composed of materials that will not affect the bioavailability and performance of the agent. As generally used herein "excipient" includes, but is not limited to surfactants, emulsifiers, emulsion stabilizers, emollients, buffers, solvents, dyes, flavors, binders, fillers, lubricants, and preservatives. Suitable excipients include those generally known in the art such as the "Handbook of Pharmaceutical Excipients", 4th Ed., Pharmaceutical Press, 2003.

Pharmaceutical compositions can optionally further contain one or more additional proteins as desired, including plasma proteins, proteases, and other biological material, so long as it does not cause adverse effects upon administration to a subject. Suitable proteins or biological material may be obtained from human or mammalian plasma by any of the purification methods known and available to those skilled in the art; from supernatants, extracts, or lysates of recombinant tissue culture, viruses, yeast, bacteria, or the like that contain a gene that expresses a human or mammalian plasma protein which has been introduced according to standard recombinant DNA techniques; or from the fluids (e.g., blood, milk, lymph, urine or the like) or transgenic animals that contain a gene that expresses a human plasma protein which has been introduced according to standard transgenic techniques.

Pharmaceutical compositions can comprise one or more pH buffering compounds to maintain the pH of the formulation at a predetermined level that reflects physiological pH, such as in the range of about 5.0 to about 8.0. The pH buffering compound used in the aqueous liquid formulation can be an amino acid or mixture of amino acids, such as histidine or a mixture of amino acids such as histidine and glycine. Alternatively, the pH buffering compound is preferably an agent which maintains the pH of the formulation at a predetermined level, such as in the range of about 5.0 to about 8.0, and which does not chelate calcium ions. Illustrative examples of such pH buffering compounds include, but are not limited to, imidazole and acetate ions. The pH buffering compound may be present in any amount suitable to maintain the pH of the formulation at a predetermined level.

Pharmaceutical compositions can also contain one or more osmotic modulating agents, i.e., a compound that modulates the osmotic properties (e.g., tonicity, osmolality and/or osmotic pressure) of the formulation to a level that is acceptable to the blood stream and blood cells of recipient individuals. The osmotic modulating agent can be an agent that does not chelate calcium ions. The osmotic modulating agent can be any compound known or available to those skilled in the art that modulates the osmotic properties of the formulation. One skilled in the art may empirically determine the suitability of a given osmotic modulating agent for use in the inventive formulation. Illustrative examples of suitable types of osmotic modulating agents include, but are not limited to: salts, such as sodium chloride and sodium acetate; sugars, such as sucrose, dextrose, and mannitol; amino acids, such as glycine; and mixtures of one or more of these agents and/or types of agents. The osmotic modulating agent(s) maybe present in any concentration sufficient to modulate the osmotic properties of the formulation.

Compositions comprising the HDAC11 inhibitors and/or SUV39H2 inhibitors described herein can contain multivalent metal ions, such as calcium ions, magnesium ions and/or manganese ions. Any multivalent metal ion that helps stabilizes the composition and that will not adversely affect recipient individuals may be used. The skilled artisan, based on these two criteria, can determine suitable metal ions empirically and suitable sources of such metal ions are known, and include inorganic and organic salts.

Other delivery systems can include time-release, delayed release or sustained release delivery systems. Such systems can avoid repeated administrations of compositions, increasing convenience to the subject and the physician. Many types of release delivery systems are available and known to those of ordinary skill in the art. They include polymer base systems such as polylactides (U.S. Pat. No. 3,773,919; European Patent No. 58,481), poly(lactide-glycolide), copolyoxalates polycaprolactones, polyesteramides, polyorthoesters, polyhydroxybutyric acids, such as poly-D-(−)-3-hydroxybutyric acid (European Patent No. 133,988), copolymers of L-glutamic acid and gamma-ethyl-L-glutamate (Sidman, K R. et at, Biopolymers 22: 547-556), poly (2-hydroxyethyl methacrylate) or ethylene vinyl acetate (Langer, ft et at, J. Biomed. Mater. Res. 15:267-277; Langer, B. Chem. Tech. 12:98-105), and polyanhydrides.

Other examples of sustained-release compositions include semi-permeable polymer matrices in the form of shaped articles, e.g., films, or microcapsules. Delivery systems also include non-polymer systems that are: lipids including sterols such as cholesterol, cholesterol esters and fatty acids or neutral fats such as mono-, di- and tri-glycerides; hydrogel release systems such as biologically-derived bioresorbable hydrogel (i.e., chitin hydrogels or chitosan hydrogels); sylastic systems; peptide based systems; wax coatings; compressed tablets using conventional binders and excipients; partially fined implants; and the like. Specific examples include, but are not limited to: (a) erosional systems in which the agent is contained in a form within a matrix, such as those described in 13.5. U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480.

Compositions including the HDAC11 inhibitor and/or SUV39H2 inhibitor described herein are particularly suitable for treating age-related retinal dysfunctions, such as age-related macular degeneration.

In one approach, the HDAC11 inhibitors and/or SUV39H2 inhibitors can be administered through an ocular device suitable for direct implantation into the vitreous of the eye. The compositions may be provided in sustained release compositions, such as those described in, for example, U.S. Pat. Nos. 5,672,659 and 5,595,760. Such devices are found to provide sustained controlled release of various compositions to treat the eye without risk of detrimental local and systemic side effects. An object of the ocular method of delivery is to maximize the amount of drug contained in an intraocular device or implant while minimizing its size in order to prolong the duration of the implant. See, e.g., U.S. Pat. Nos. 5,378,475; 6,375,972, and 6,756,058 and U.S. Publications 20050096290 and 200501269448. Such implants may be biodegradable and/or biocompatible implants, or may be non-biodegradable implants.

Biodegradable ocular implants are described, for example, in U.S. Patent Publication No. 20050048099. The implants may be permeable or impermeable to the active agent, and may be inserted into a chamber of the eye, such as the anterior or posterior chambers or may be implanted in the sclera, transchoroidal space, or an avascularized region exterior to the vitreous. Alternatively, a contact lens that acts as a depot for compositions of the invention may also be used for drug delivery.

In some embodiments, the implant may be positioned over an avascular region, such as on the sclera, so as to allow for transcleral diffusion of the drug to the desired site of treatment, e.g., the intraocular space and macula of the eye. Furthermore, the site of transcleral diffusion is preferably in proximity to the macula. Examples of implants for delivery of a composition of the invention include, but are not limited to, the devices described in U.S. Pat. Nos. 3,416,530; 3,828,777; 4,014,335; 4,300,557; 4,327,725; 4,853,224; 4,946,450; 4,997,652; 5,147,647; 164,188; 5,178,635;

5,300,114; 5,322,691; 5,403,901; 5,443,505; 5,466,466; 5,476,511; 5,516,522; 5,632,984; 5,679,666; 5,710,165; 5,725,493; 5,743,274; 5,766,242; 5,766,619; 5,770,592; 5,773,019; 5,824,072; 5,824,073; 5,830,173; 5,836,935; 5,869,079, 5,902,598; 5,904,144; 5,916,584; 6,001,386; 6,074,661; 6,110,485; 6,126,687; 6,146.366; 6,251,090; and 6,299,895, and in WO 01/30323 and WO 01/28474, all of which are incorporated herein by reference.

Other approaches for ocular delivery include the use of liposomes to target the HDAC11 inhibitors and/or SUV39H2 inhibitors described herein to the retina, retinal pigment epithelial cells, and/or Bruch's membrane. For example, the HDAC11 inhibitors and/or SUV39H2 inhibitors may be complexed with liposomes, and this liposome complex injected into patients with an ocular disorder, such as AMD, using intravenous injection or subretinal injection to direct the HDAC11 inhibitor and/or SUV39H2 inhibitor/liposome complex to the desired ocular tissue or cell. Directly injecting the liposome complex into the proximity of the retina, retinal pigment epithelial cells, or Bruch's membrane can also provide for targeting of the complex with some forms of ocular disorders, such as AMD. In a specific embodiment, the HDAC11 inhibitor and/or SUV39H2 inhibitor can be administered via intraocular sustained delivery (such as VITRASERT or ENVISION). In a specific embodiment, the c HDAC11 inhibitors and/or SUV39H2 inhibitors can be delivered by posterior subtenons injection. In another specific embodiment, microemulsion particles containing the HDAC11 inhibitors and/or SUV39H2 inhibitors can be delivered to ocular tissue to take up lipid from the retina, Bruchs membrane, or retinal pigment epithelial cells.

Compositions including the HDAC11 inhibitors and/or SUV39H2 inhibitors described herein may also be delivered topically. For topical delivery, the compositions are provided in any pharmaceutically acceptable excipient that is approved for ocular delivery. Preferably, the composition is delivered in drop form to the surface of the eye. For some applications, the delivery of the composition relies on the diffusion of the compounds through the cornea to the interior of the eye.

In one example, an HDAC11 inhibitor and/or SUV39H2 inhibitor described herein can be provided in an ophthalmic preparation that can be administered to the subject's eye. The ophthalmic preparation can contain the HDAC11 inhibitors and/or SUV39H2 inhibitors in a pharmaceutically acceptable solution, suspension or ointment. Some variations in concentration will necessarily occur, depending on the particular HDAC11 inhibitor and/or SUV39H2 inhibitor employed, the condition of the subject to be treated and the like, and the person responsible for treatment will determine the most suitable concentration for the individual subject. The ophthalmic preparation can be in the form of a sterile aqueous solution containing, if desired, additional ingredients, for example, preservatives, buffers, tonicity agents, antioxidants, stabilizers, nonionic wetting or clarifying agents, and viscosity increasing agents.

The compositions including the HDAC11 inhibitors and/or SUV39H2 inhibitors described herein, as described above, can be administered to the subject in effective amounts. The effective amount will depend upon the mode or administration, the particular condition being treated and the desired outcome. It may also depend upon the stage of the condition, the age and physical condition of the subject, the nature of concurrent therapy, if any, and like factors well known to the medical practitioner. For therapeutic applications, it is that amount sufficient to achieve a medically desirable result.

The treatment methods can include administering to the subject a therapeutically effective amount of the HDAC11 inhibitors and/or SUV39H2 inhibitors described herein. Generally, pharmaceutical compositions for use in the methods described herein can have a therapeutically effective amount of the HDAC11 inhibitors and/or SUV39H2 inhibitors in a dosage in the range of 0.01 to 1,000 mg/kg of body weight of the subject, and more preferably in the range of from about 10 to 100 mg/kg of body weight of the patient.

In some embodiments, a therapeutically effective amount of the HDAC11 inhibitors and/or SUV39H2 inhibitors administered to the subject is an amount effective to improve or preserve visual function, inhibit photoreceptor cell death, and/or improve or preserve retinal structure.

In some embodiments, the improvement or preservation in visual function include an improvement or preservation of photopic electroretinogram (ERG) response. In other embodiments, the improvement or preservation in retinal structure is an improvement or preservation of outer nuclear layer (ONL) thickness.

With respect to a subject suffering from age-related retinal dysfunction, an effective amount is amount effective or sufficient to improve or preserve visual function, inhibit photoreceptor cell death, and/or improve or preserve retinal structure. Generally, doses of the HDAC11 inhibitors and/or SUV39H2 inhibitors would be from about 0.01 mg/kg per day to about 1000 mg/kg (e.g., 0.01, 0.05, 0.1, 0.25, 0.5, 1.0, 5, 10, 15, 20, 25) per day. It is expected that doses ranging from about 50 to about 2000 mg/kg (e.g., 50, 100, 200, 250, 500, 750, 1000, 1250, 1500, 1750, 2000) will be suitable. Lower doses will result from certain forms of administration, such as intravitreal or ocular administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of a composition including the compounds described herein.

In some embodiments, the HDAC11 inhibitors and/or SUV39H2 inhibitors described herein can be administered to the subject at early stage or intermediate stage of the age-related retinal dysfunction, such age-related macular degeneration (AMD). The age-related macular degeneration (AMD) course can be conveniently divided into three stages, i.e., the early stage, intermediate stage, and late stage.

In the early stage, AMD involves medium-sized drusen deposits seen upon eye examination. No pigment changes are present, and there is usually no vision loss at this stage of the disease. Early-stage AMD is usually detected upon a routine eye examination by an ophthalmologist (eye doctor) or other healthcare provider. During this initial stage, an ophthalmologist can detect drusen, long before symptoms occur.

Intermediate-stage AMD involves large drusen, or multiple medium-sized drusen and/or pigment changes are present in one or both eyes, upon examination by the ophthalmologist. Pigment changes, also called retinal pigment epithelium (RPE) disturbances, can lead to vision loss. Studies suggest that the RPE is where macular degeneration starts to occur. The function of the RPE is to absorb light and transport nutrients to the retinal cells. Symptoms that commonly occur during the intermediate stage could include subtle changes in vision, but for many people, there are no symptoms yet. Some people begin to see black or gray spots in the center of their visual field, or they may have trouble adjusting from a location with bright light to a dim area.

Late-stage AMD involves either the wet form of AMD or dry AMD; in the late-stage either form of AMD causes distortion of vision and/or vision loss. The wet form of AMD progresses much faster than the dry form, and wet AMD is much more likely to cause vision loss. When central vision loss begins, objects may appear distorted or blurry at first, but in the late-stage of the disease, objects in the middle of your line of vision cannot be seen at all, although in the peripheral field (side vision) objects are usually still visible, but it may be difficult to decipher what they are. In the late-stage of the disease, a person may no longer be able to recognize faces and although they may still have peripheral (side) vision, they may be considered legally blind.

In one embodiment, a subject is diagnosed as having symptoms of age-related retinal dysfunction (such as impaired vision, drusen deposition, pigment changes, light sensitivity, tunnel vision, and loss of peripheral vision to total loss of vision), and then a disclosed compound is administered. In another embodiment, a subject may be identified as being at risk for developing age-related retinal dysfunction (risk factors may include family history or testing positive for a rhodopsin mutation), and then a disclosed compound is administered. In yet another embodiment, a subject may be diagnosed as having age-related retinal dysfunction and then a disclosed compound is administered. In another embodiment, a subject may be identified as being at risk for developing other forms of retinal degeneration in photoreceptor cells, and then the disclosed compound is administered. In some embodiments, a compound is administered prophylactically. In some embodiments, a subject has been diagnosed as having the disease before retinal damage is apparent. In some embodiments, a human subject may know that he or she is in need of the retinal generation treatment or prevention.

In some embodiments, a subject may be monitored for the extent of retinal degeneration. A subject may be monitored in a variety of ways, such as by eye examination, dilated eye examination, fundoscopic examination, visual acuity test, and/or biopsy. Monitoring can be performed at a variety of times. For example, a subject may be monitored after a compound is administered. The monitoring can occur, for example, one day, one week, two weeks, one month, two months, six months, one year, two years, five years, or any other time period after the first administration of a compound. A subject can be repeatedly monitored. In some embodiments, the dose of a compound may be altered in response to monitoring.

Another strategy for treating a subject suffering from an age-related retinal dysfunction is to administer a therapeutically effective amount of the HDAC11 inhibitors and/or SUV39H2 inhibitors described herein along with a therapeutically effective amount of an additional anti-retinal degeneration agent or therapy. Examples of anti-retinal degeneration agents or therapies include but are not limited to supplements, such as vitamin A, DHA, and lutien, as well as optic prosthetic devices, gene therapy mechanisms and retinal sheet transplantations.

Those of skill in the art will recognize that the best treatment regimens for using any of the HDAC11 inhibitors and/or SUV39H2 inhibitors to age-related retinal dysfunction can be straightforwardly determined. This is not a question of experimentation, but rather one of optimization, which is routinely conducted in the medical arts. In vivo studies in nude mice often provide a starting point from which to begin to optimize the dosage and delivery regimes. The frequency of injection will initially be once a week, as has been done in some mice studies. However, this frequency might be optimally adjusted from one day to every two weeks to monthly, depending upon the results obtained front the initial clinical trials and the needs of a particular patient.

Human dosage amounts can initially be determined by extrapolating from the amount of the HDAC11 inhibitor and/or SUV39H2 inhibitor used in mice, as a skilled artisan recognizes it is routine in the art to modify the dosage for humans compared to animal models. In certain embodiments it is envisioned that the dosage may vary an amount ranging from about 10-1000 mg (e.g., about 20 mg-1,000 mg, 30 mg-1,000 mg, 40 mg-1,000 mg, 50 mg-1,000 mg, 60 mg-1,000 mg, 70 mg-1,000 mg, 80 mg-1,000 mg, 90 mg-1,000 mg, about 10-900 mg, 10-800 mg, 10-700 mg, 10-600 mg, 10-500 mg, 100-1000 mg, 100-900 mg, 100-800 mg, 100-700 mg, 100-600 mg, 100-500 mg, 100-400 mg, 100-300 mg, 200-1000 mg, 200-900 mg, 200-800 mg, 200-700 mg, 200-600 mg, 200-500 mg, 200-400 mg, 300-1000 mg, 300-900 mg, 300-800 mg, 300-700 mg, 300-600 mg, 300-500 mg, 400 mg-1,000 mg, 500 mg-1,000 mg, 100 mg-900 mg, 200 mg-800 mg, 300 mg-700 mg, 400 mg-700 mg, and 500 mg-600 mg). In some embodiments, the compound is present in an amount of or greater than about 10 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg. In some embodiments, the HDAC11 inhibitor and/or SUV39H2 inhibitor is present in an amount of or less than about 1000 mg, 950 mg, 900 mg, 850 mg, 800 mg, 750 mg, 700 mg, 650 mg, 600 mg, 550 mg, 500 mg, 450 mg, 400 mg, 350 mg, 300 mg, 250 mg, 200 mg, 150 mg, or 100 mg.

In other embodiments, a therapeutically effective dosage amount of the HDAC11 inhibitor and/or SUV39H2 inhibitor may be, for example, about 0.001 mg/kg weight to 500 mg/kg weight, e.g., from about 0.001 mg/kg weight to 400 mg/kg weight, from about 0.001 mg/kg weight to 300 mg/kg weight, from about 0.001 mg/kg weight to 200 mg/kg weight, from about 0.001 mg/kg weight to 100 mg/kg weight, from about 0.001 mg/kg weight to 90 mg/kg weight, from about 0.001 mg/kg weight to 80 mg/kg weight, from about 0.001 mg/kg weight to 70 mg/kg weight, from about 0.001 mg/kg weight to 60 mg/kg weight, from about 0.001 mg/kg weight to 50 mg/kg weight, from about 0.001 mg/kg weight to 40 mg/kg weight, from about 0.001 mg/kg weight to 30 mg/kg weight, from about 0.001 mg/kg weight to 25 mg/kg weight, from about 0.001 mg/kg weight to 20 mg/kg weight, from about 0.001 mg/kg weight to 15 mg/kg weight, from about 0.001 mg/kg weight to 10 mg/kg weight.

In still other embodiments, a therapeutically effective dosage amount of the HDAC11 inhibitor and/or SUV39H2 inhibitor may be, for example, about 0.0001 mg/kg weight to 0.1 mg/kg weight, e.g. from about 0.0001 mg/kg weight to 0.09 mg/kg weight, from about 0.0001 mg/kg weight to 0.08 mg/kg weight, from about 0.0001 mg/kg weight to 0.07 mg/kg weight, from about 0.0001 mg/kg weight to 0.06 mg/kg weight, from about 0.0001 mg/kg weight to 0.05 mg/kg weight, from about 0.0001 mg/kg weight to about 0.04 mg/kg weight, from about 0.0001 mg/kg weight to 0.03 mg/kg weight, from about 0.0001 mg/kg weight to 0.02 mg/kg weight, from about 0.0001 mg/kg weight to 0.019 mg/kg weight, from about 0.0001 mg/kg weight to 0.018 mg/kg weight, from about 0.0001 mg/kg weight to 0.017 mg/kg weight, from about 0.0001 mg/kg weight to 0.016 mg/kg weight, from about 0.0001 mg/kg weight to 0.015 mg/kg weight, from about 0.0001 mg/kg weight to 0.014 mg/kg weight, from about 0.0001 mg/kg weight to 0.013 mg/kg weight, from about 0.0001 mg/kg weight to 0.012 mg/kg weight, from about 0.0001 mg/kg weight to 0.011 mg/kg weight, from about 0.0001 mg/kg weight to 0.01 mg/kg weight, from about 0.0001 mg/kg weight to 0.009 mg/kg weight, from about 0.0001 mg/kg weight to 0.008 mg/kg weight, from about 0.0001 mg/kg weight to 0.007 mg/kg weight, from about 0.0001 mg/kg weight to 0.006 mg/kg weight, from about 0.0001 mg/kg weight to 0.005 mg/kg weight, from about 0.0001 mg/kg weight to 0.004 mg/kg weight, from about 0.0001 mg/kg weight to 0.003 mg/kg weight, from about 0.0001 mg/kg weight to 0.002 mg/kg weight. In some embodiments, the therapeutically effective dose may be 0.0001 mg/kg weight, 0.0002 mg/kg weight, 0.0003 mg/kg weight, 0.0004 mg/kg weight, 0.0005 mg/kg weight, 0.0006 mg/kg weight, 0.0007 mg/kg weight, 0.0008 mg/kg weight, 0.0009 mg/kg weight, 0.001 mg/kg weight, 0.002 mg/kg weight, 0.003 mg/kg weight, 0.004 mg/kg weight, 0.005 mg/kg weight, 0.006 mg/kg weight, 0.007 mg/kg weight, 0.008 mg/kg weight, 0.009 mg/kg weight, 0.01 mg/kg weight, 0.02 mg/kg weight, 0.03 mg/kg weight, 0.04 mg/kg weight, 0.05 mg/kg weight, 0.06 mg/kg weight, 0.07 mg/kg weight, 0.08 mg/kg weight, 0.09 mg/kg weight, or 0.1 mg/kg weight. The effective dose for a particular individual can be varied (e.g., increased or decreased) over time, depending on the needs of the individual.

In some embodiments, a therapeutically effective dosage of the HDAC11 inhibitor and/or SUV39H2 inhibitor may be a dosage of 10 μg/kg/day, 50 μg/kg/day, 100 μg/kg/day, 250 μg/kg/day, 500 μg/kg/day, 1000 μg/kg/day or more. In various embodiments, the amount of the HDAC11 inhibitor and/or SUV39H2 inhibitor or pharmaceutical salt thereof is sufficient to provide a dosage to a patient of between 0.01 μg/kg and 10 μg/kg; 0.1 μg/kg and 5 μg/kg; 0.1 μg/kg and 1000 μg/kg; 0.1 μg/kg and 900 μg/kg; 0.1 μg/kg and 900 μg/kg; 0.1 μg/kg and 800 μg/kg; 0.1 μg/kg and 700 μg/kg; 0.1 μg/kg and 600 μg/kg; 0.1 μg/kg and 500 μg/kg; or 0.1 μg/kg and 400 μg/kg.

Treatment according to the methods described herein can be altered, stopped, or re-initiated in a subject depending on the status of age-related retinal dysfunction. Treatment can be carried out as intervals determined to be appropriate by those skilled in the art. For example, the administration can be carried out 1, 2, 3, or 4 times a day. In some embodiments, the compounds can be administered after induction of retinal degeneration has occurred.

In one aspect, a pharmaceutical composition comprising an effective amount of the HDAC11 inhibitor and/or SUV39H2 inhibitor is administered at least twice. In another aspect, a pharmaceutical composition is administered at least five times. In yet another aspect, a pharmaceutical composition is administered at least 10 times. One of ordinary skill in the art can determine how often to administer the composition based on the particular disease or disorder being treated or how the subject has responded to prior treatments.

As discussed above, the HDAC11 inhibitor and/or SUV39H2 inhibitor may be administered to a subject in order to treat or prevent macular degeneration and other forms of retinal disease whose etiology involves progressive photoreceptor degeneration in the central retina and epigenetic changes in chromatin accessibility resulting from environmental exposure and chronic stress. Other diseases, disorders, or conditions characterized by such photoreceptor degeneration in the central retina and epigenetic changes in chromatin accessibility may be similarly treated.

In one embodiment, a subject is diagnosed as having symptoms of macular degeneration, and then a disclosed compound is administered. In another embodiment, a subject may be identified as being at risk for developing macular degeneration (risk factors include a history of smoking, age, female gender, and family history), and then a disclosed compound is administered. In another embodiment, a subject may have dry AMD in both eye, and then a disclosed compound is administered. In another embodiment, a subject may have wet AMD in one eye but dry AMD in the other eye, and then a disclosed compound is administered. In yet another embodiment, a subject may be diagnosed as having Stargardt disease and then a disclosed compound is administered. In another embodiment, a subject is diagnosed as having symptoms of other forms of retinal disease whose etiology involves photoreceptor degeneration in the central retina and epigenetic changes in chromatin accessibility, and then the compound is administered. In another embodiment, a subject may be identified as being at risk for developing other forms of retinal disease whose etiology involves photoreceptor degeneration in the central retina and epigenetic changes in chromatin accessibility, and then the disclosed compound is administered. In some embodiments, a compound is administered prophylactically. In some embodiments, a subject has been diagnosed as having the disease before retinal damage is apparent. In some embodiments, a human subject may know that he or she is in need of the macular generation treatment or prevention.

In some embodiments, the disclosed methods may be combined with other methods for treating or preventing macular degeneration or other forms of retinal disease whose etiology involves photoreceptor degeneration in the central retina and epigenetic changes in chromatin accessibility. For example, a patient may be treated with more than one therapy for one or more diseases or disorders. For example, a patient may have one eye afflicted with dry form AMD, which is treated with a compound of the invention, and the other eye afflicted with wet form AMD, which is treated with, e.g., photodynamic therapy.

The invention is further illustrated by the following example, which is not intended to limit the scope of the claims.

EXAMPLE

In this Example, we show that a photosensitive mouse model of acute stress-induced photoreceptor degeneration can recapitulate the epigenetic hallmarks of human AMD. Global epigenomic profiling was accomplished by employing an Assay for Transposase-Accessible Chromatin using Sequencing (ATAC-Seq), which revealed an association between decreased chromatin accessibility and stress-induced photoreceptor cell death in our mouse model. The epigenomic changes induced by light damage include reduced euchromatin and increased heterochromatin abundance, resulting in transcriptional and translational dysregulation that ultimately drives photoreceptor apoptosis and an inflammatory reactive gliosis in the retina. We further show that pharmacological inhibition of histone deacetylase 11 (HDAC11) and suppressor of variegation 3-9 homolog 2 (SUV39H2), key histone-modifying enzymes involved in promoting reduced chromatin accessibility, ameliorated light damage in our mouse model, supporting a causal link between decreased chromatin accessibility and photoreceptor degeneration, thereby elucidating a potential new therapeutic strategy to combat AM.

Materials and Methods

Animals

Male and female Abca4$^{-/-}$Rdh8$^{-/-}$ mice at 6 to 8 weeks of age were used for the current study. These mice were maintained on a pigmented C57BL/6 background, and age-matched C57BL/6 mice from The Jackson Laboratory were used as wild-type controls. All mice were housed and maintained in a 12-hour light (≤150 lux)/12-hour dark cyclic environment in the University Laboratory Animal Resources center at the University of California, Irvine (UCI) School of Medicine. Bright light-induced retinal damage was generated by exposing photosensitive Abca4$^{-/-}$Rdh8$^{-/-}$ mice to white light delivered at 10,000 lux (150-W spiral lamp, Commercial Electric, Cleveland, OH) for 30 min. Mice were dark-adapted 24 h prior to photobleaching, and pupils were dilated with 1% ophthalmic tropicamide 30 min prior to light exposure. Mocetinostat (MedChemExpress #HY-12164, 60 mg/kg bw) and OTS186935 (AdooQ Bioscience #A18632, 60 mg/kg bw) were dissolved in DMSO and administered in a total volume of 50 μL by intraperitoneal injection 30 min prior to light exposure. All animal handling procedures and experimental protocols were approved by the Institutional Animal Care and Use Committee at UCI and conformed to recommendations of both the American Veterinary Medical Association (AVMA) Panel on Euthanasia and the Association for Research in Vision and Ophthalmology.

Live in Vivo Retinal Imaging

Mice were anesthetized by intraperitoneal injection of ketamine (20 mg/mL) with xylazine (1.75 mg/mL) at a dose of 5 μL/g bw, and pupils were dilated with 1% tropicamide prior to imaging. Ultrahigh-resolution spectral domain OCT (Bioptigen, Research Triangle Park, NC) was performed for cross-sectional imaging of mouse retinas, as described previously. Briefly, five frames of OCT images were acquired in the B-mode and then averaged. For quantitative measurements of photoreceptor viability, ONL thickness was measured in the InVivoVue software at a distance of 0.45 mm from the optic nerve head in the temporal retina, where the most severe damage is found in bright light-exposed Abca4$^{-/-}$Rdh8$^{-/-}$ mice. SLO (Heidelberg Engineering, Heidelberg, Germany) was also performed for whole fundus imaging of mouse retinas, and images were acquired in the autofluorescence mode, as previously described.

ATAC Sequencing

Fresh retina and RPE/choroid tissues were harvested from photosensitive Abca4$^{-/-}$Rdh8$^{-/-}$ mice and dissociated into single cells using the Worthington Papain Dissociation System (Lakewood, NJ). For nuclear extraction, cells (50-75 k) were lysed by adding 50 μL of ice-cold cell lysis buffer (10 mM Tris Cl pH 7.4, 10 mM NaCl, 3 mM $MgCl_2$) containing 0.03% IGEPAL and protease inhibitors (1 tablet per 7 mL of lysis buffer) and mixing 3 times by pipetting. Cells were then immediately spun down at 500 g for 10 min and washed with 150 μL of ice-cold lysis buffer without IGEPAL and protease inhibitors. For tagmentation, cell nuclei were incubated with 2.5 μL enzyme in 50 μL total volume at 37° C. in a thermocycler (Illumina Nextera DNA library prep kit, #FC1211030). DNA was cleaned up using the MinElute PCR purification kit (#28006, Qiagen) and eluted in 10 μL of EB buffer. Tagmented DNA was amplified, and the number of PCR cycles were calculated by following a previously described protocol. PCR products (10 μL) were run on a 1.5% agarose gel to confirm expected DNA band pattern. PCR products were then cleaned by double-sized selection using Ampure beads (Agencout AMPure XP, Beckman Coulter, #A63880) to remove large and small DNA fragments. This was performed by using 1:0.5 and 1:1.6 ratios of sample to Ampure beads (v/v). Completed ATAC-Seq libraries were then analyzed by Fragment Bioanalyzer and sequenced for paired-end 75 cycles using the NextSeq 500 system with ~400-500 million reads per run, yielding approximately 45-50 million reads per sample.

ATAC-Seq Differential Chromatin Accessibility Analysis

Adaptors were removed using Trimmomatic. ATAC-seq reads were aligned to the mouse genome (GRCm38) using Bowtie2 with default parameters. After filtering the read for mitochondrial DNA, the Y chromosome duplicate reads were removed using the Picard tools MarkDuplicates program. ATAC-seq peak regions of each sample were called using MACS2 with the parameters -nomodel -shift 100 -extsize 200. All peak files were combined together, with overlapping peaks merged into a single peak. We identified 63,018 peaks from retina samples and 19,950 peaks from the RPE/choroid samples. The top 25 percent of the peaks by signal strength were plotted using R. Integrative genomics viewer was used to visualize peak intensity for individual genes. DeepTools2 was used to create BigWig files. The BigWig files were merged together for each time point to create heatmaps for the peak values from the top half of the peaks by signal strength. The circos plots were created using circlize. MDS plots were created from the values of all peaks using edgeR.

Retina and RPE Extraction for RNA-Seq

Fresh retina and RPE tissues were harvested from photosensitive Abca4$^{-/-}$Rdh8$^{-/-}$ mice according to published protocols. Under a dissecting microscope, spring scissors were used to puncture the eye and remove the cornea, iris, and lens. The remaining eyecup had 4 radial incisions made every 90 degrees, resulting in a flat and open eye cup. The retina was then gently removed using curved tweezers and placed in a 1.5 mL microcentrifuge tube containing RNAlater (Qiagen, Hilden, Germany) The RPE-containing eyecup was placed in a 1.5 mL microcentrifuge tube containing RNAprotect (Qiagen). The second eye was processed identically and pooled with the first eye from the same mouse. Total RNA from RPE cells was isolated using the simultaneous RPE cell isolation and RNA stabilization (SRIRS) method. Briefly, the tube containing RNAprotect with the 2 pooled RPE/choroid eyecups was agitated in 10 min intervals for 20 min at RT. After the second agitation, the eyecups were removed to minimize choroid contamination, with dissociated RPE cells remaining in solution. Retina and RPE samples in RNAlater and RNAprotect, respectively, were stored at 4° C. for up to one week.

RNA Sequencing

Retina tissue samples were removed from the RNAlater solution and placed in a fresh 1.5 mL microcentrifuge tube.

RPE samples were centrifuged for 5 min at 700 g and the supernatant was then discarded. Total cellular RNA isolation was performed with the miRNAeasy micro kit with an optional DNase step, per the manufacturer's protocol (Qiagen, Hilden, Germany). RNA samples were sent to the Transcriptomics and Deep Sequencing Core (Johns Hopkins University, Baltimore, MD) for library preparation and sequencing. Briefly, mRNA was polyA-selected from total RNA (100-150 ng per sample) and subjected for library preparation by following the Illumina TruSeq Stranded mRNA Library Prep Kit instructions. Libraries were then pooled and sequenced for paired-end 150 cycles in the Illumina NextSeq 500 system, yielding approximately 45-50 million raw reads per library.

RNA-Seq Differential Gene Expression Analysis

Alignment of sequences to the genome was completed using STAR version 2.5.3, Ensembl GRCm38 was used for STAR mapping and read counts were generated using the featureCounts function of Rsubread. Gene transcripts with 1≥CPM in 4 or more replicates were considered expressed and used in all downstream analyses. Differential gene expression analysis was performed using edgeR. Ggplot2 was used to create the correlation plots. The R package VennDiagram was used to create the Venn diagram. Gene set enrichment analysis was performed using the Gene Ontology (GO) functional annotation clustering method of DAVID 6.8 to determine the biological function of differentially expressed genes. Seurat was used to determine cell type markers and perform the pseudo-scRNA-Seq analysis by cross-referencing an unpublished wild-type C57BL/6 murine retina scRNA-Seq dataset. For each time point analyzed in the bulk RNA-seq data, the DE genes up- or down-regulated relative to non-bleached controls were used to create a "meta gene" from the scRNA-Seq dataset, which was a collective sum of the values for all the up- or down-regulated DE genes. The collective up and down meta genes generated were then used through standard Seurat tools to highlight meta gene expression in individual cells on the UMAP plot.

Preparation of Tissue Lysates for Western Blotting Analysis

Fresh retina and RPE were harvested from study mice as described previously. Briefly, samples from both eyes of the same mouse were pooled together and homogenized in RIPA buffer supplemented with a protease and phosphatase inhibitor cocktail (Roche, Basel, Switzerland). Posterior eye cups (sclera-choroid-RPE) were incubated on ice for 20 min with frequent agitation to dissociate the RPE monolayer into solution, then the remainder of the eye cups were removed prior to sonication, vortex, and centrifugation at 21,000 g for 15 min at 4° C. Proteins were size-fractionated on 4-12% Bis-Tris Nu-PAGE gels (Invitrogen, Carlsbad, CA) and transferred to nitrocellulose membranes. The membranes were incubated in Intercept blocking solution (LI-COR, Lincoln, NE) for 1 h at RT, followed by primary antibodies targeting H3K27ac (1:1000, Cell Signaling #8173), H3K9me3 (1:1000, Abcam #8898), and GAPDH (1:1000, Cell Signaling #2118) overnight at 4° C. Membranes were washed with PBS containing 0.1% Tween-20 and incubated with an infrared dye (IR)-labeled goat anti-rabbit secondary antibody (1:5000, LI-COR #926-32211) for 1 h at RT. The blots were imaged, and IR signals were quantified using a LI-COR Odyssey Fc imaging system.

Immunofluorescence Microscopy

Mice were euthanized in a $CO_2$ chamber prior to enucleation. For IF staining of retina and RPE flat mounts, the cornea and lens were first dissected out, then the remaining neural retina was separated from the RPE-containing posterior eye cup and both were fixed in 4% paraformaldehyde for 30 min Retina and RPE-containing eye cups were then flattened by making long radial cuts and mounted on glass slides (Superfrost Plus, Fisher Scientific). For both IHC and flat mount IF staining, slides were incubated in a blocking buffer containing 5% FBS, 1% BSA, and 0.2% Triton X-100 in PBS for 2 h at RT. Slides were then incubated with a primary antibody targeting H3K9me3 (1:100, Abcam #8898) overnight at 4° C., followed by a 1 h incubation with a fluorescent goat anti-rabbit secondary antibody (1:250, Invitrogen #A11037). F-actin was labeled by FITC-phalloidin (1:200, Invitrogen #A12379) co-incubated with secondary antibody for 1 h at RT. Fluorescence microscopy images were obtained on a Keyence BZ-X810 fluorescent microscope.

Statistical Analyses

Results were collected from at least three mice for each experimental group unless otherwise indicated. Data from at least three independent experiments were presented as mean±standard error of the mean (SEM). Statistical significance was determined by the Student's t test, where differences with $P<0.05$ were considered significant. Fold change, false discovery rate (FDR), and Pearson's correlation coefficient were calculated in the R platform (https://www.R-project.org).

Results

Global Chromatin Accessibility Changes in Phototoxicity

Figure 2A:
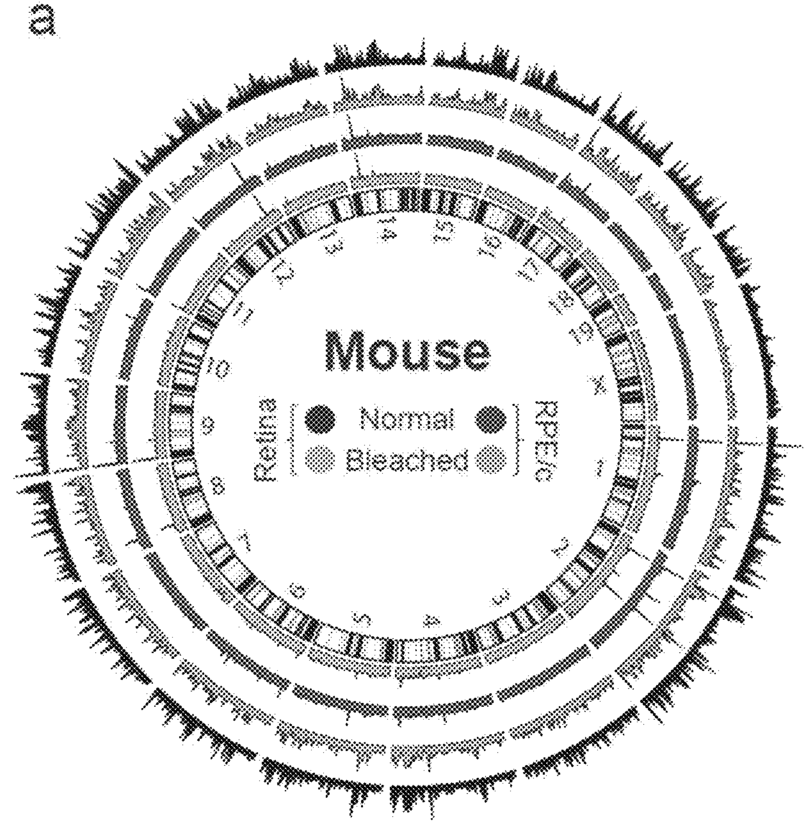
FIGS. 2(A-C) illustrate plots showing epigenetic landscape of chromatin accessibility in retina and RPE/choroid. Circos plots showing genome-wide chromatin accessibility as ATAC-Seq peaks in retina and RPE/choroid (RPE/c) of A) photosensitive $Abca4^{-/-}Rdh8^{-/-}$ (dKO) mice reared under normal lighting conditions and 1 day after exposure to bright light stress (bleached), and B) humans with and without AMD (generated from raw human sequencing data deposited in NCBI's Gene Expression Omnibus (GEO) under accession number GSE99287). C) Chromatin accessibility changes induced by photobleaching. Average ATAC-Seq signal in key genes for non-bleached (NB, n=5) and bleached dKO retina 6 hours (n=3) and 1 day (n=6) after bright light exposure. TSS, transcriptional start site; kb, kilobases.
Figure 2B:
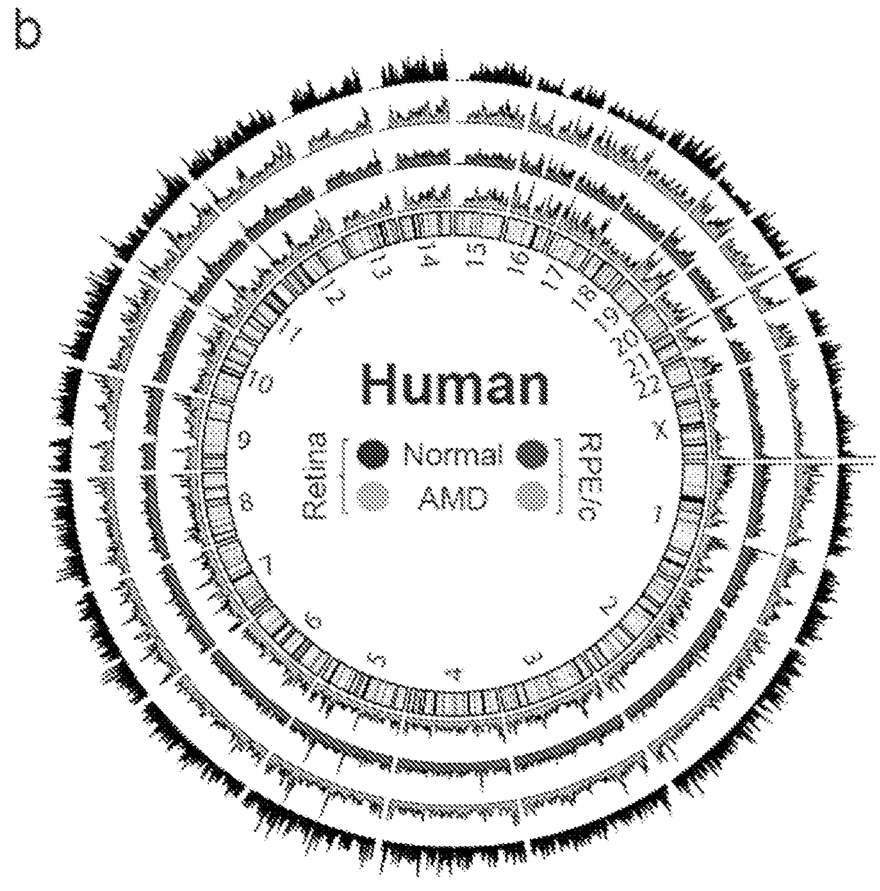
Figure 2C:
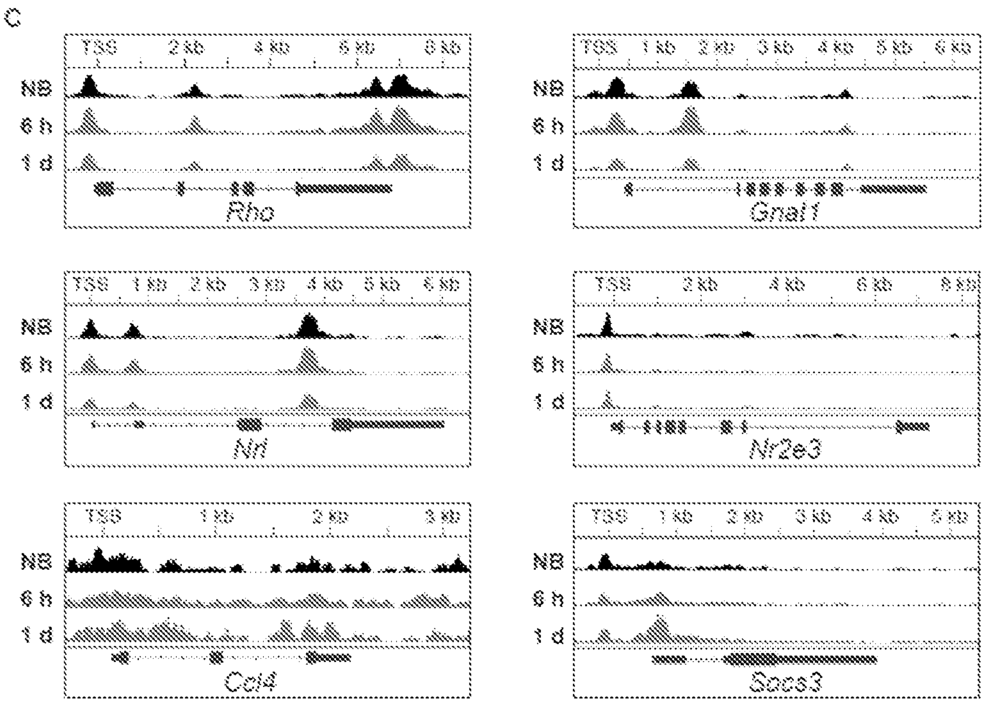

In this study, we characterized the epigenetic phenotype of our photosensitive dKO mouse model using ATAC-Seq, in order to globally profile chromatin accessibility in the retina and RPE/choroid. Samples were processed in triplicate or as specified for each experimental condition, and in total 63,018 high-confidence peaks representing open chromatin regions were identified in the retina and 19,950 high-confidence peaks were identified in the RPE/choroid. In dKO mice subjected to bright light exposure, we observed on average a broad decrease in peak intensity with diffusion into intergenic regions of the genome in both retina and RPE/choroid one day after photobleaching (FIG. 2A), resembling the global reduction in accessibility of open chromatin regions previously characterized in clinical cases of AMD (FIG. 2B). Notably, the key photoreceptor genes Rho, Gnat1, Nrl, and Nr2e3 exhibited a mixed initial response at 6 hours after light exposure, which stabilized into an overall decrease in peak intensity by one day after photobleaching (FIG. 2C). In contrast, key inflammatory response genes Ccl4 and Socs3 actually exhibited an increase in peak intensity following photobleaching, consistent with the upregulation of these genes seen in the inflammatory reactive gliosis that follows light-induced photoreceptor degeneration.

Figure 3E:
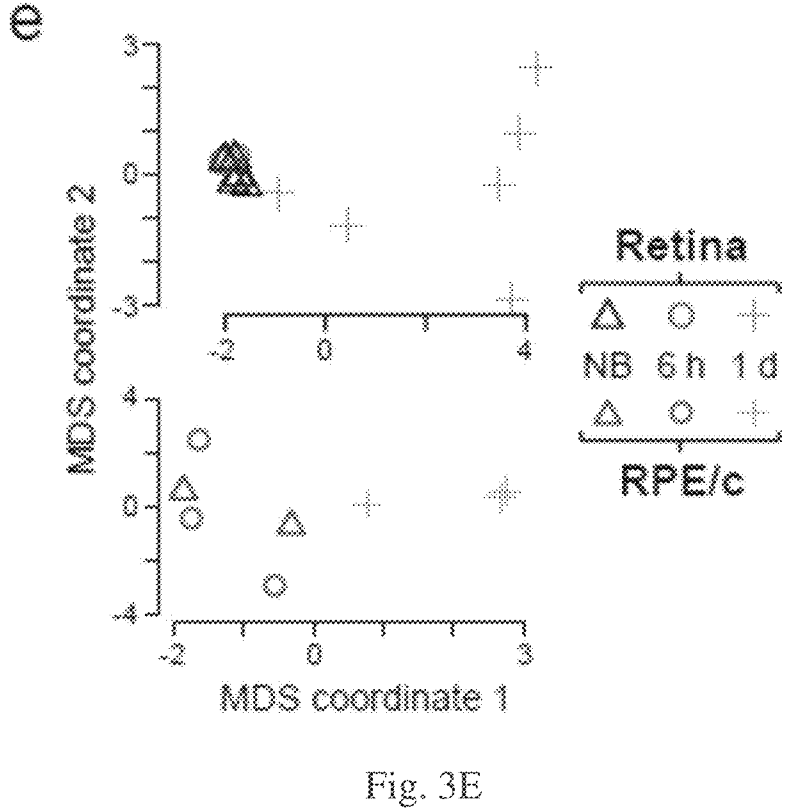
FIGS. 3(A-D) illustrate images and plots showing chromatin accessibility changes in light-damaged retina. A) SLO images (top) demonstrate the time course of induction of retinal pathology (autofluorescent spots) in the fundus of photosensitive $Abca4^{-/-}Rdh8^{-/-}$ (dKO) mice 6 hours to 1/3/7 days after exposure to bright light stress, as compared to non-bleached (NB) dKO and wild-type (WT) mice. SLO scale bars, 1 mm OCT images (bottom) were also obtained from these mice, and the thickness of the photoreceptor-containing outer nuclear layer (ONL, yellow asterisk) is quantified in B), exhibiting complete degeneration in the dKO mice by 7 days post-bleach. OCT scale bars, 50 μm. INL, inner nuclear layer; GCL, ganglion cell layer. n=3 per group. C) Global decrease of chromatin accessibility in retina and RPE/choroid (RPE/c) 1 day after photobleaching relative to non-bleached dKO mice. Each data point (left panel) represents one ATAC-Seq peak, and the population of reduced peaks is highlighted in blue in the density curve (right panel) and quantified as a percentage of all ATAC-Seq peaks. D) Global heat map of open chromatin regions in non-bleached dKO mice, compared to 6 hours and 1 day after bright light exposure. Each row (bottom panel) represents one ATAC-Seq peak, and the degree of chromatin accessibility is represented by color. Peaks are aligned at the center of regions spanning 2 kilobases (kb). The total ATAC-Seq signal (normalized counts) of all peaks combined is shown in the top panel. D) Multidimensional scaling (MDS) of all retina and RPE/choroid samples. Non-bleached (n=5 for retina, n=2 for RPE/c) and bleached dKO mice 6 hours (n=3 for retina, n=3 for RPE/c) and 1 day (n=6 for retina, n=3 for RPE/c) after light exposure cluster into groups with distinct ATAC-Seq profiles.

In order to visualize the progression of photoreceptor degeneration in mice, we utilized Scanning Laser Ophthalmoscopy (SLO) and Optical Coherence Tomography (OCT) to image the fundus and cross-sections of the retina, respectively (FIG. 3A). In photobleached dKO mice, SLO imaging revealed characteristic autofluorescent spots associated with phototoxicity and reactive inflammation, which became increasingly apparent in the days following light damage. OCT imaging revealed a concomitant degeneration of the photoreceptor-containing outer nuclear layer (ONL) in bleached dKO mice relative to both wild-type (WT) and non-bleached (NB) controls, with full degeneration of the ONL evident at 7 days after photobleaching (FIG. 3B). At one day after light exposure, the majority of ATAC-Seq peaks, 93.7% in the retina and 55.6% in the RPE/choroid of dKO mice, were reduced in signal intensity (FIG. 3C), representative of a global decrease in accessibility of open chromatin regions. This global decrease occurred gradually, with total ATAC signal intensity decreasing in a time-dependent manner following light damage (FIG. 3D). As expected, this analysis showed that the chromatin accessibility changes induced by bright light stress result in distinct and reproducible epigenomic profiles (FIG. 3E).

Epigenomic Changes Manifest in the Transcriptome

Figure 4A:
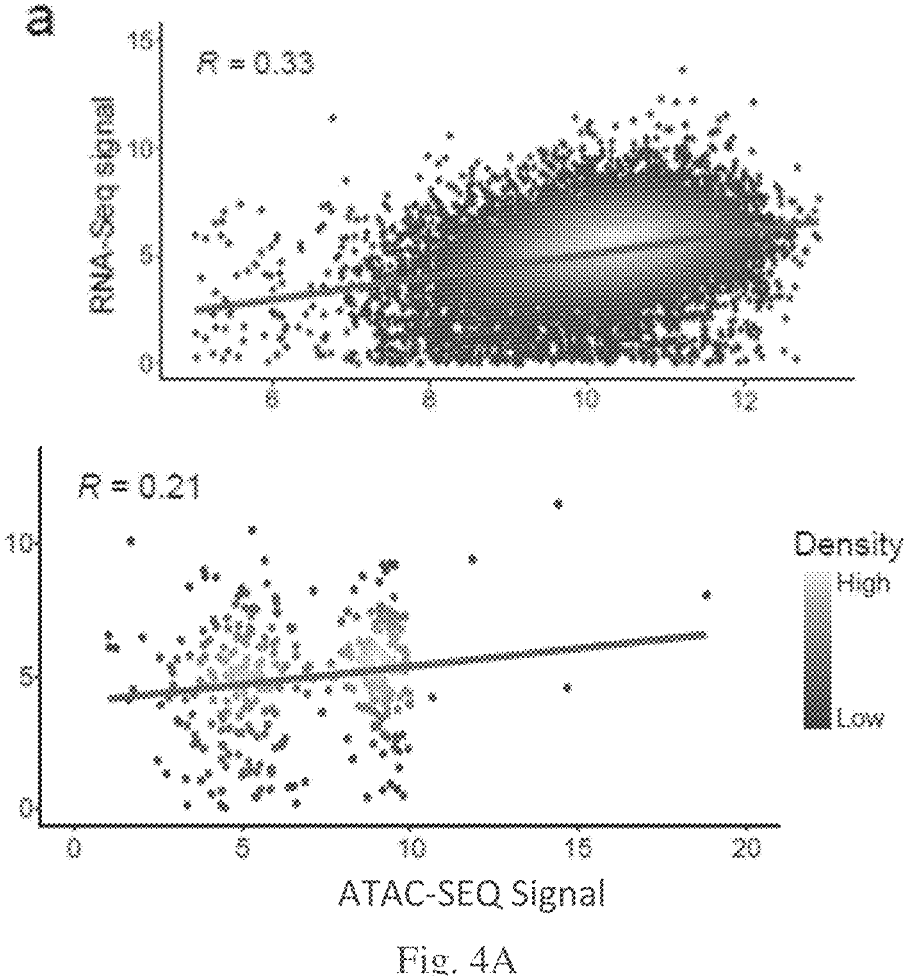
FIGS. 4(A-D) illustrate plots showing the transcriptome reflects epigenetic changes associated with photoreceptor degeneration. A) Relationship between chromatin accessibility (ATAC-Seq signal intensity) and gene expression (RNA-Seq signal intensity) in retina and RPE/choroid (RPE/c) of unbleached dKO mice. Pearson's product-moment correlation constant (R) is displayed on the graph (P value<0.0001). B) Multidimensional scaling (MDS) of all retina and RPE/choroid samples. Non-bleached (NB) and bleached dKO mice cluster into groups with distinct RNA-Seq profiles. n=4 per group for all NB, 1 d, and 3 d samples. n=3 per group for all 6 h samples. C) Differentially expressed (DE) genes in retina and RPE/choroid 6 h, 1 day, and 3 days after photobleaching (BL). Each data point represents one RNA-Seq peak, and the total sum of significantly upregulated and downregulated DE genes is quantified in D) at 6 h, 1 day, and 3 days post-bleach, respectively; DE genes total 852, 1839, and 712 in retina and 9, 216, and 13 in RPE/choroid.
Figure 4B:
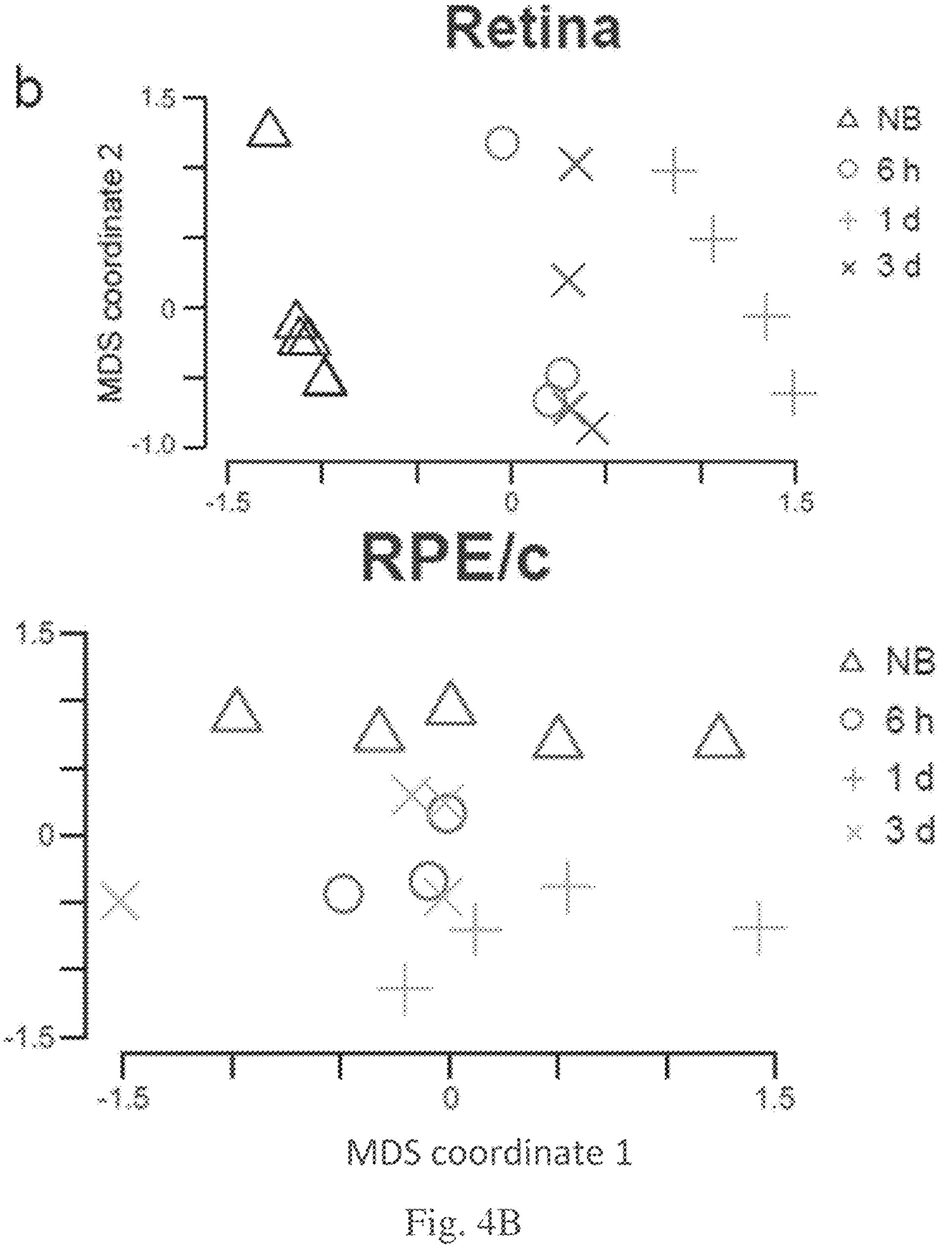
Figure 4C:
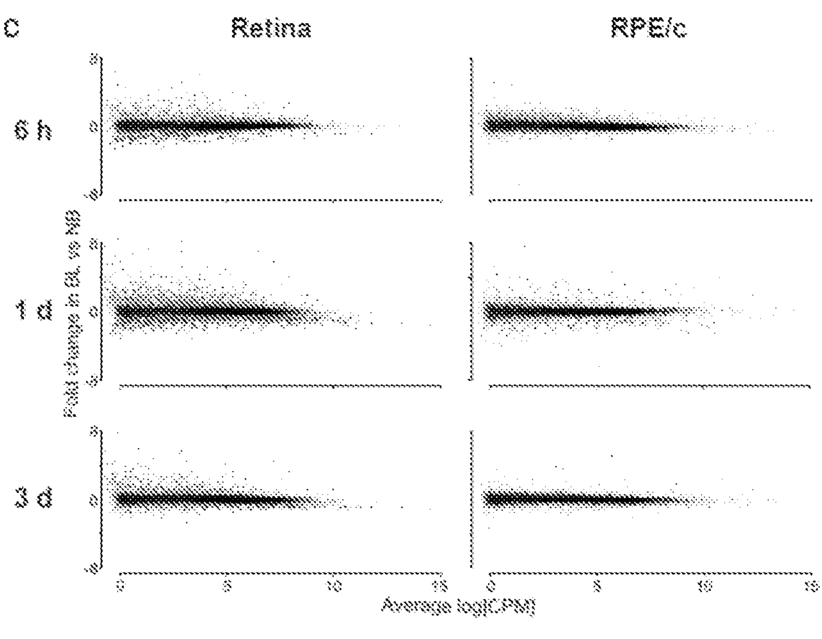
Figure 4D:
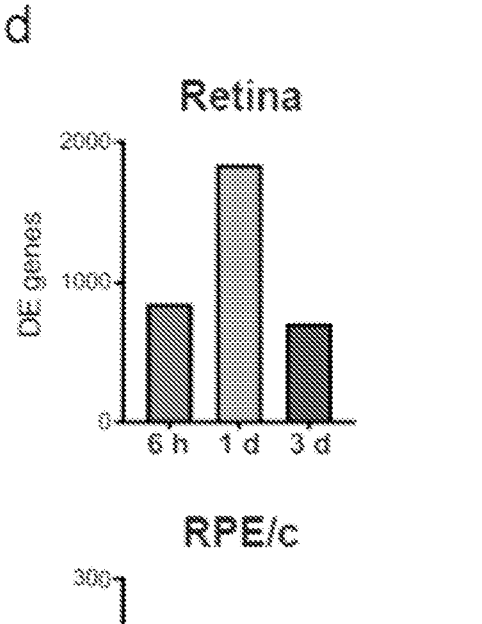

In order to assess how changes at the epigenomic level are reflected in the transcriptome, we utilized next-generation RNA-sequencing (RNA-Seq) and performed a correlation analysis. In non-bleached dKO mice, the retina exhibited a higher degree of correlation between ATAC-Seq and RNA-Seq data than the RPE/choroid, with Pearson correlation coefficients (R) of 0.33 and 0.21, respectively (FIG. 4A). Taken together, this positive correlation supports a direct relationship between chromatin accessibility and gene transcription. Indeed, MDS analysis of our RNA-Seq data suggests a programmed transcriptional response to bright light stress that results in distinct and reproducible transcriptomic profiles (FIG. 4B). Using differential gene expression analysis, we identified statistically significant differentially expressed (DE) genes in the retina and RPE/choroid of dKO mice at 6 hours, 1 day, and 3 days after light damage, and found that the majority of transcriptomic changes occur in the retina, with the total number of DE genes approximately ten-fold higher than in RPE/choroid (FIG. 4*c-d*). Moreover, in both retina and RPE/choroid, the majority of transcriptomic changes occurred one day after photobleaching.

Figure 5A:
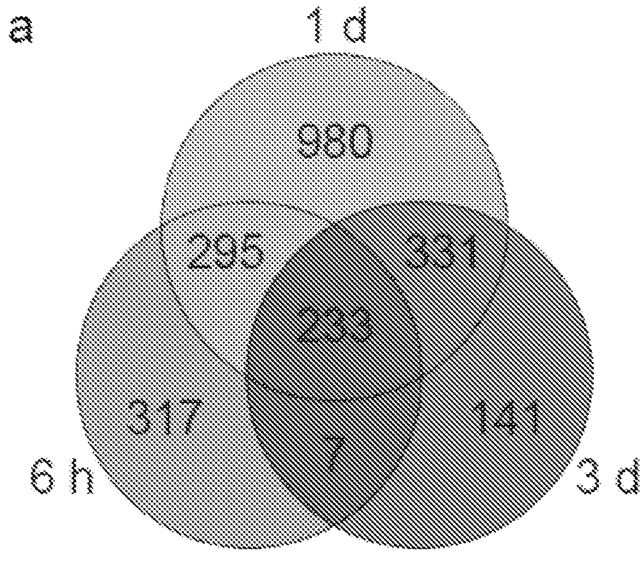
FIGS. 5(A-D) illustrate diagrams, graphs, and plots showing transcriptomic analysis reveals biological pathways underlying photoreceptor degeneration. A) Venn diagram of the total numbers of differentially expressed (DE) genes in retina 6 h, 1 day, and 3 days after photobleaching, relative to non-bleached dKO mice. B) Global transcriptome gene set enrichment analysis identifies top biological pathways associated with bright-light induced damage in retina of dKO mice at indicated time points after photobleaching. C) Proportion of cell type-specific DE genes at corresponding time points after photobleaching. Majority of stress-induced transcriptomic changes shift from photoreceptors (early) to glia (late), suggesting a late-onset inflammatory reactive gliosis. DE genes were cross-referenced against a single-cell RNA-Seq (scRNA-seq) database of the top 50 genes unique to each retinal cell type and are represented as a percentage of the total number of DE genes that are cell-type specific at each time point. D) Pseudo-scRNA-seq analysis maps of upregulated (red) and downregulated (blue) DE genes in distinct retinal cell types. Uniform Manifold Approximation and Projection (UMAP) non-linear dimensionality reduction was used to cluster individual cells with similar transcriptomic profiles and assign cell types based on expression of unique marker genes. Cell types exhibiting highest degree of differential gene expression at each time point are labeled. As, Astrocyte; Pc, Pericyte; EC, Endothelial Cell.
Figure 5B:
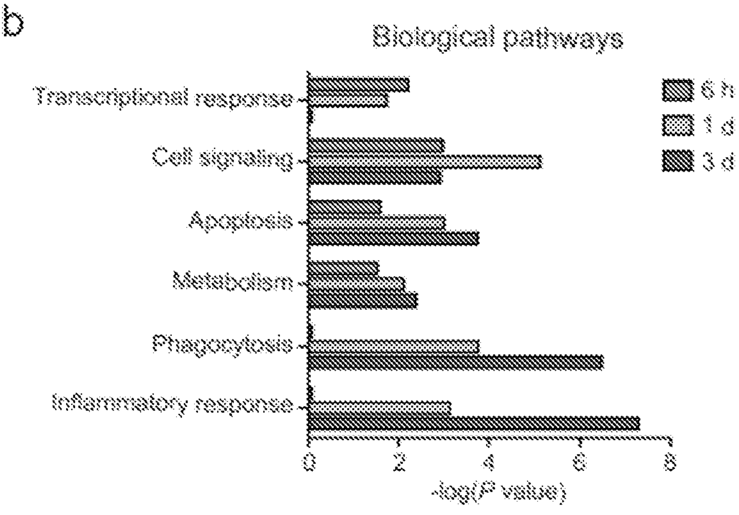
Figure 5C:
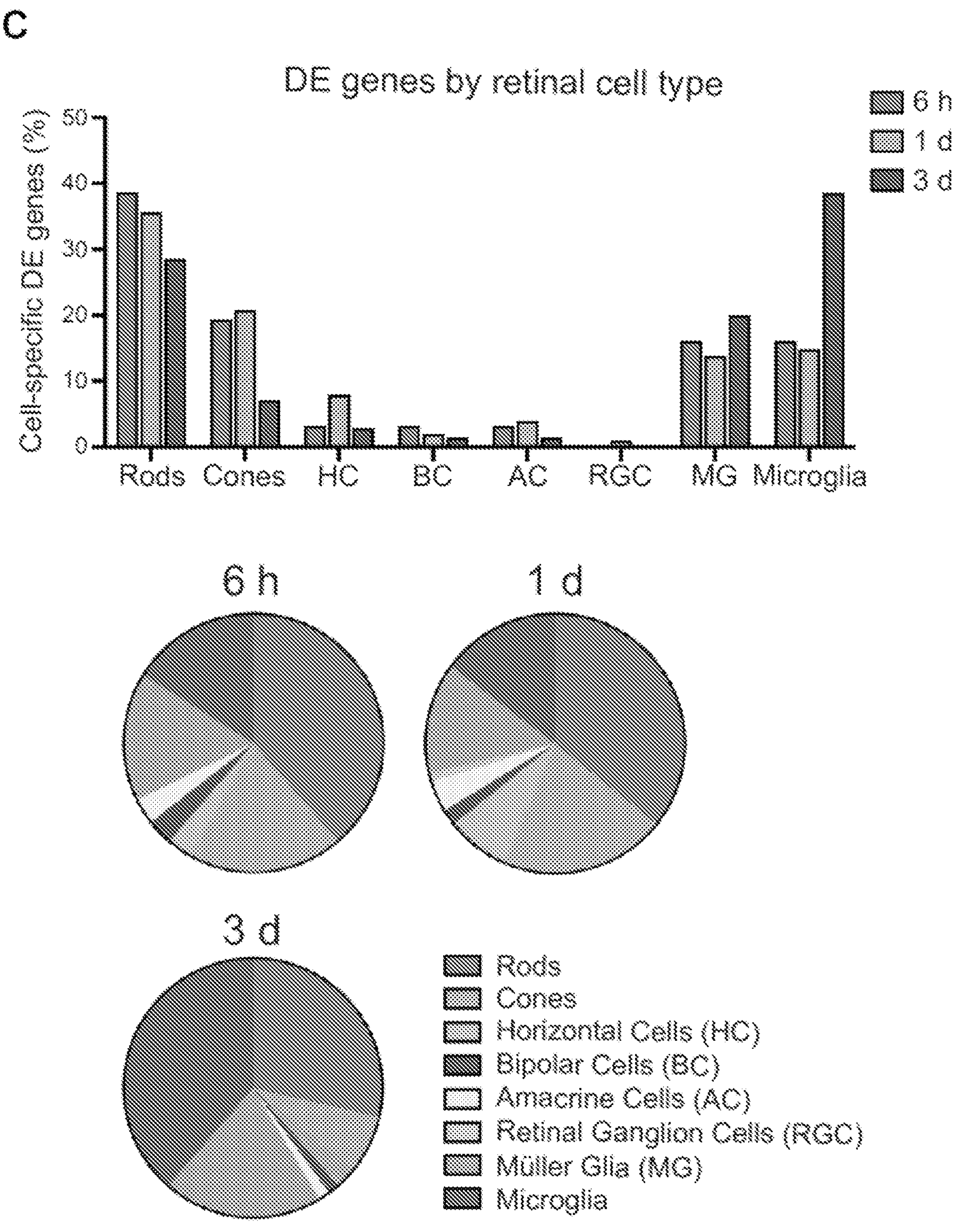
Figure 5D:
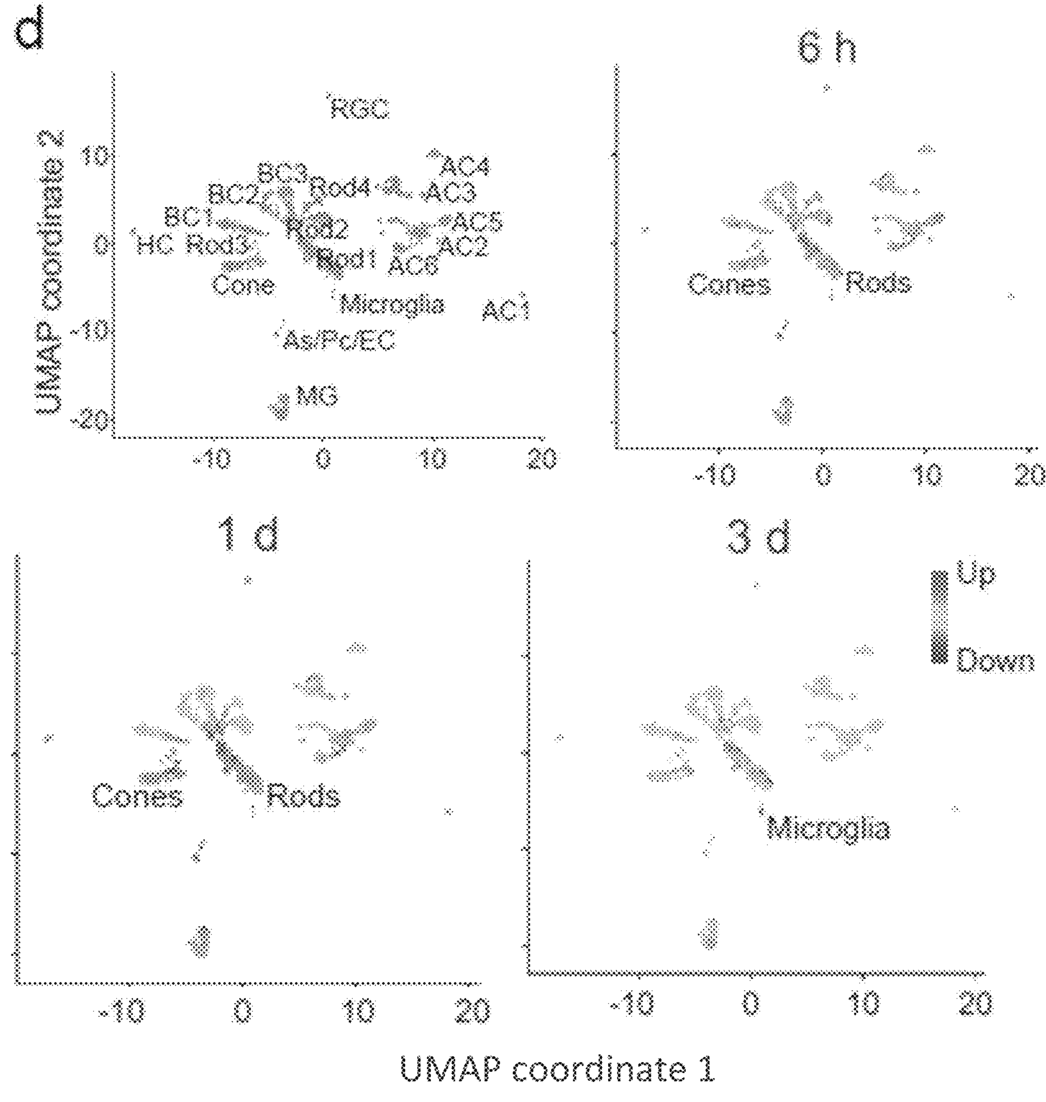

To elucidate the pertinent biological pathways involved in the progression of photoreceptor degeneration, we first generated a Venn diagram to quantify the total number of DE genes unique to each post-bleach time point. At 6 hours, 1 day, and 3 days post-bleach, 317, 980, and 141 unique DE genes were identified in the retina of dKO mice, respectively (FIG. 5A). We then performed gene set enrichment analysis on these unique genes, which revealed early enrichment in transcriptional activation, cell signaling, apoptosis, and metabolism pathways, followed by delayed enrichment in phagocytosis and inflammatory response pathways (FIG. 5B). Upon closer inspection of specific DE genes, we observed early downregulation of key photoreceptor genes Nrl, Nr2e3, Rho, and Gnat1, followed by upregulation of key immune response genes Ccl4, Socs3, Ifi204, Ddx58, Cfi, C3, Nfkb2, Gfap, and Cd68. Moreover, upregulation of gliosis markers GFAP and CD68 at the protein level was visually confirmed by immunohistochemistry analysis of retinal cross-sections. Taken together, these results suggest an initial transcriptional response that predominates in light-damaged photoreceptors, followed by a delayed inflammatory response mediated by retinal glia. To investigate this possibility, Seurat was used on a generic wild-type murine retina single cell RNA-Seq (scRNA-Seq) dataset to determine the top 50 marker genes unique to each retinal cell type, and the DE genes identified from each post-bleach time point were matched to the marker genes and quantified as a percentage of the total number of cell-type specific genes for each time point. Indeed, this analysis revealed the majority of stress-induced transcriptomic changes shift from rod and cone photoreceptors (early) to Müller glia and microglia (late), with a minority of transcriptomic changes occurring in amacrine, horizontal, and bipolar cells of the inner retina (FIG. 5C). By integrating Uniform Manifold Approximation and Projection (UMAP) non-linear dimensionality reduction analysis of the scRNA-Seq data with our dKO mouse RNA-Seq data, we employed a novel methodology henceforth known as "pseudo-scRNA-Seq" to map DE genes to individual cells on a UMAP plot for each post-bleach time point (FIG. 5D). As expected from our epigenomic data, this analysis revealed mixed up- and down-regulation of transcription at 6 hours, followed by a more uniform downregulation in photoreceptors at 1-day post-bleach, and delayed upregulation occurring in activated microglia 3 days after light damage.

Chromatin Remodeling Drives Phototoxicity

Figure 6A:
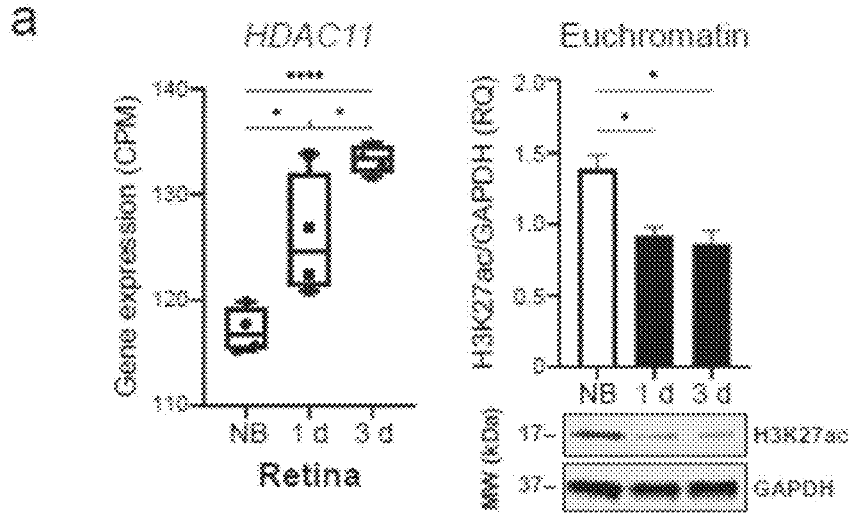
FIGS. 6(A-C) illustrate plots and images showing histone modifications associated with decreased chromatin accessibility. A) Expression of HDAC11 in retina (left panel), measured in counts per million (CPM). Increased expression corresponds to histone modifications that decrease chromatin accessibility (n=4 per group, $^*P<0.05$, $^{****}P<0.0001$). Euchromatin marker H3K27ac is decreased in dKO mice 1 day and 3 days after photobleaching (right panel). Representative Western blot (WB) analysis and quantification of H3K27ac levels, expressed as relative quantity (RQ), in retina of non-bleached (NB) and bleached dKO mice (n=3 per group, $^*P<0.05$). B) Expression of SUV39H2 in RPE/choroid (RPE/c) (left panel). Heterochromatin marker H3K9me3 is increased in dKO mice 1 day and 3 days after photobleaching (right panel). Representative WB analysis and quantification of H3K9me3 levels in RPE/c of non-bleached and bleached dKO mice. All P values were calculated by the unpaired t test. C) RPE flat mount immunofluorescence microscopy. F-actin labels RPE cell borders, nuclei are labeled by DAPI, and H3K9me3 is a marker for heterochromatin foci. 60× magnification is of boxed region shown in 20× merged window. Increased heterochromatin staining is observed in dKO mice one day after photobleaching. Scale bars, 50 μm.
Figure 6B:
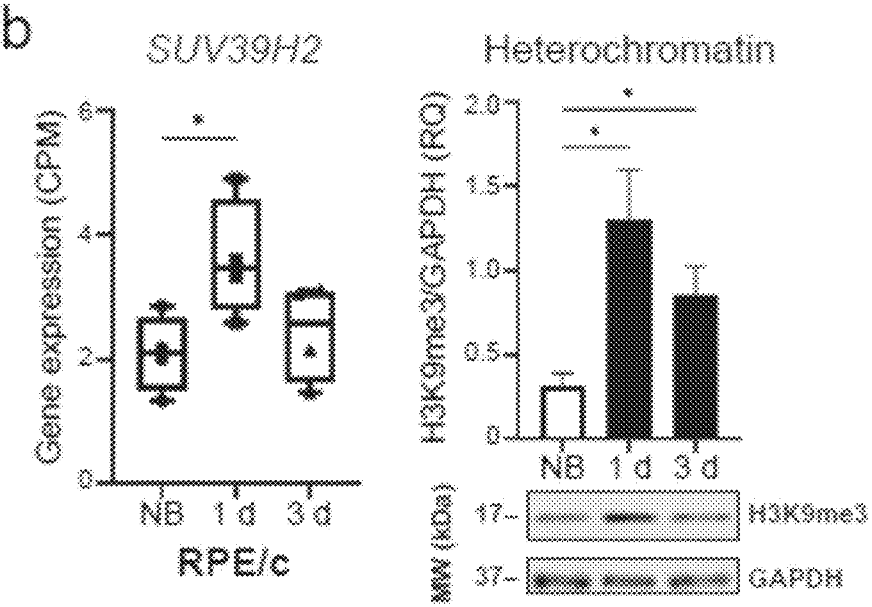
Figure 6C:
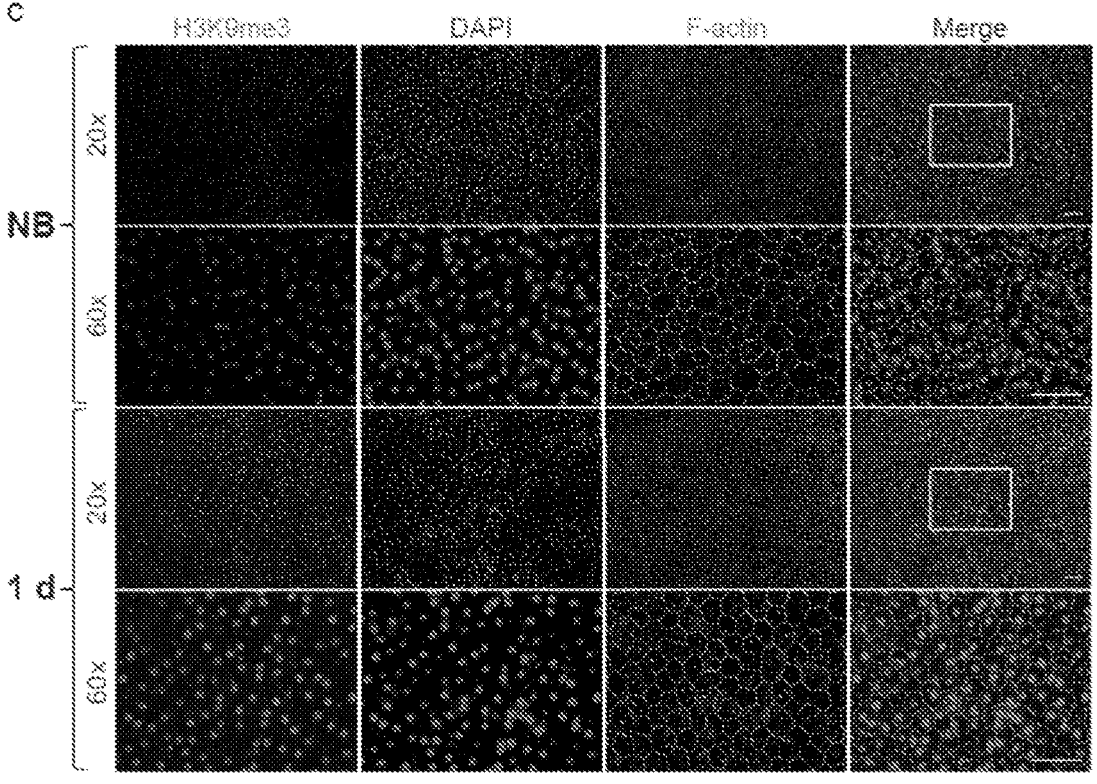

Among the many DE genes identified in our study, we first narrowed our focus on DE genes encoding histone-modifying enzymes that could drive the observed changes in chromatin accessibility. From this list, we identified HDAC11, which encodes an enzyme that functions to deacetylate histones, thereby promoting reduced chromatin accessibility. Notably, upregulation of this gene, along with decreased histone acetylation, have also been observed in clinical cases of dry AMD. In bleached dKO mice, we observed statistically significant upregulation of HDAC11 both 1 day and 3 days after light damage in the retina (FIG. 6A), which corresponded with decreased protein abundance of H3K27ac, an acetylated histone marker for open chromatin regions (euchromatin). Likewise, in the RPE/choroid at 1-day post-bleach, we observed statistically significant upregulation of SUV39H2, which encodes a methyltransferase that trimethylates the K9 residue of histone 3, thereby promoting formation of highly condensed, inaccessible regions of chromatin (heterochromatin). Indeed, by quantitative Western blot analysis, we observed a concomitant increase in protein abundance of H3K9me3, a marker for heterochromatin, in the RPE/choroid of bleached dKO mice compared to non-bleached controls (FIG. 6B). In order to visualize the heterochromatin formation contributing to reduced chromatin accessibility, we prepared retina and RPE flat mounts for immunofluorescence microscopy and observed increased H3K9me3 signal in both retina and RPE (FIG. 6C) of dKO mice at 1 d after photobleaching. Taken together, these results demonstrate that the global reduction of chromatin accessibility induced by bright light stress involves effectors that inhibit euchromatin while promoting heterochromatin formation.

Figure 7A:
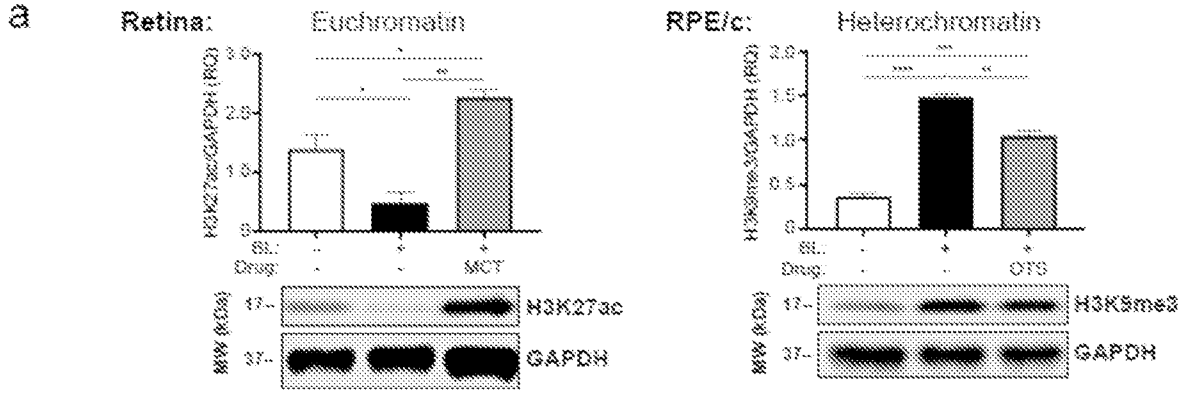
FIGS. 7(A-D) illustrate graphs and images showing pharmacological interventions that attenuate stress-induced chromatin remodeling ameliorate photoreceptor degeneration. A) Representative Western blot (WB) analysis and quantification of H3K27ac and H3K9me3 levels, expressed as relative quantity (RQ), in retina and RPE/choroid (RPE/c) of non-bleached (BL −) and 1 d post-bleach (BL +) dKO mice treated with intraperitoneal injection of DMSO vehicle (Drug −), Mocetinostat (MCT) at a dose of 60 mg/kg bw, or OTS186935 (OTS) at a dose of 60 mg/kg bw. B) Immunohistochemistry analysis of retinal cross-sections reveals broadly increased H3K9me3 staining throughout the retina of dKO mice 1 d after photobleaching relative to non-bleached controls, which is attenuated in bleached OTS-treated mice relative to DMSO vehicle-treated mice. H3K9me3 is a marker for heterochromatin foci, nuclei are labeled by DAPI, and peanut agglutinin (PNA) labels cone photoreceptors. Scale bars, 50 μm. C) SLO (top) and OCT (bottom) imaging reveals light-induced retinal pathology in dKO mice is ameliorated by MCT or OTS treatment, and the thickness of the photoreceptor-containing outer nuclear layer (ONL, yellow asterisk) is quantified in D). SLO and OCT images were acquired from live dKO mice 7 d after photobleaching. SLO scale bars, 1 mm OCT scale bars, 50 μm. INL, inner nuclear layer; GCL, ganglion cell layer. n=3 per group, $^*P<0.05$, $^{}P<0.01$, $^{*}P<0.001$, $^{****}P<0.0001$.
Figure 7B:
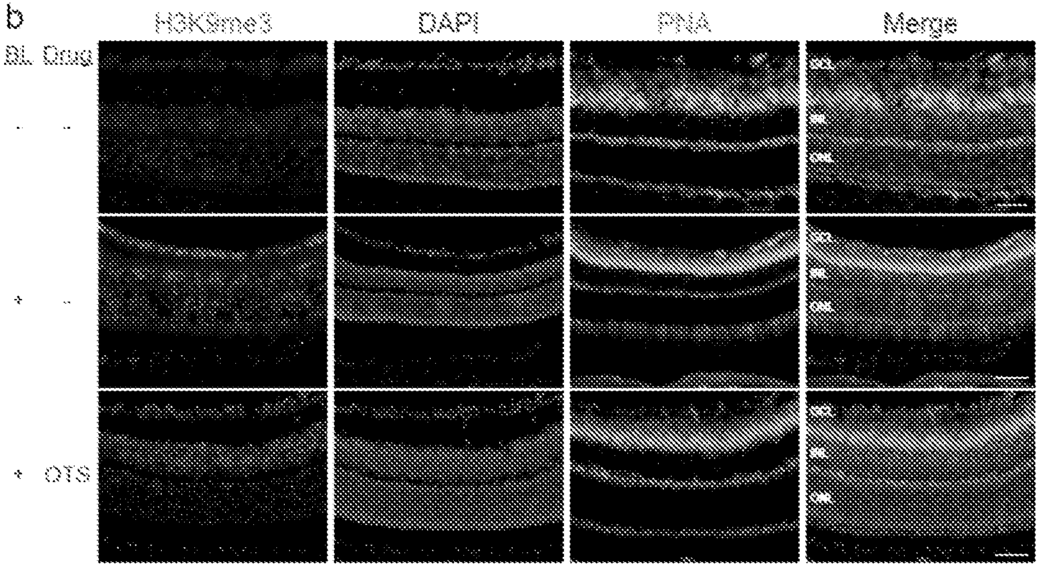
Figure 7C:
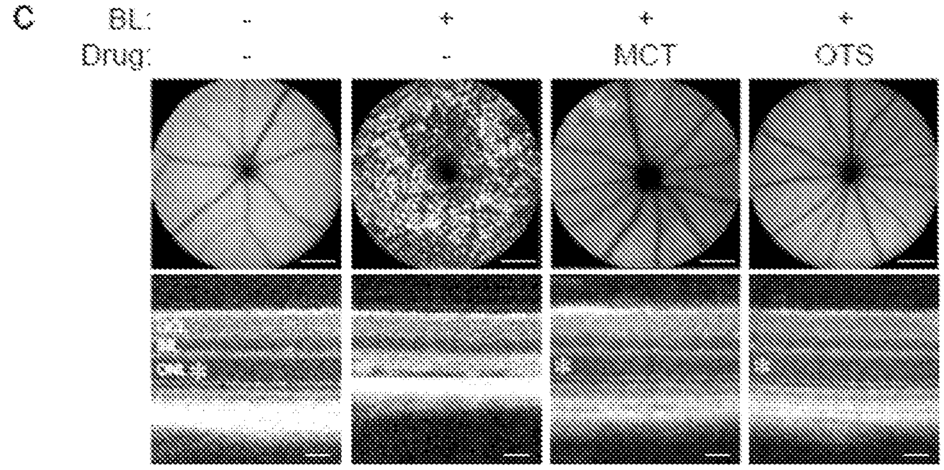
Figure 7D:
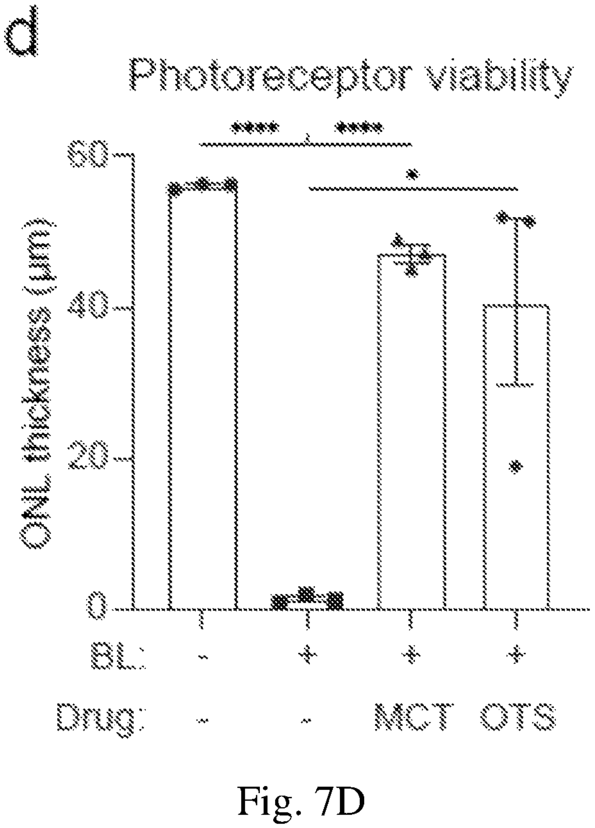

Having identified the correlation between reduced chromatin accessibility and photoreceptor degeneration in our mouse model, we next sought to investigate whether this chromatin remodeling could play a causative role in driving phototoxicity. Knowing that HDAC11 and SUV39H2 are upregulated in photobleached dKO mice, we reasoned that pharmacological inhibition of these enzymes would provide protection from light damage if reduced chromatin accessibility were indeed a driver of phototoxicity. By quantitative Western blot analysis, we first confirmed that intraperitoneal administration (60 mg/kg bw) of Mocetinostat (MCT), a pharmacological inhibitor of HDAC11, rescues the stress-induced reduction in euchromatin abundance observed in the retina of photobleached dKO mice (FIG. 7A). Likewise, we confirmed that intraperitoneal administration (60 mg/kg bw) of OTS186935 (OTS), a selective inhibitor of SUV39H2, attenuates the stress-induced increase in heterochromatin abundance observed in the RPE/choroid of bleached dKO mice. In order to visualize the effect of SUV39H2 inhibition on heterochromatin formation throughout the retina of dKO mice, we prepared retinal cross-sections for immunohistochemistry analysis and found that the widespread increase in H3K9me3 signal induced by photobleaching was attenuated by OTS therapy, particularly in the photoreceptor-containing outer nuclear layer (FIG. 7B). With confirmation that these pharmacological interventions indeed mitigate the global reduction of chromatin accessibility induced by bright light stress, we performed SLO and OCT imaging and found that either MCT or OTS therapy alone was sufficient to ameliorate stress-induced retinal pathology in photobleached dKO mice (FIG. 7C-D). Altogether, these findings demonstrate proof of concept in support of a causal relationship between decreased chromatin accessibility and photoreceptor degeneration.

In this Example, we investigated stress-induced retinal pathology in photosensitive mice and ascertained three insights on the pathogenesis of photoreceptor degeneration. The first pertains to how chromatin accessibility changes on a global level in the context of light damage. We found that upon bright light exposure, both the retina and RPE/choroid exhibit a global decrease in accessibility of open chromatin regions, as evidenced by a gradual, time-dependent reduction in total ATAC signal. Secondly, we demonstrated the relationship between changes at the epigenomic level and how they manifest in the transcriptome, observing a programmed transcriptional response to bright light stress involving cross-talk between different retinal cell types and a transition from an initial response in photoreceptors to a delayed inflammatory reactive gliosis. Lastly, we identified key histone modifications induced by bright light stress that reduce euchromatin while promoting heterochromatin formation, thereby contributing to the changes in global chromatin accessibility observed in phototoxicity.

In early stages of embryonic development, cellular differentiation results from the interplay between heritable epigenetic modifications and spatiotemporally regulated production of cell type-specific transcription factors (TFs). Cells are able to distinguish their identity through what is known as epigenetic memory, while maintaining a level of plasticity that enables restoration of tissue homeostasis after injury and exposure to other environmental stimuli over time. Rod and cone photoreceptors, which are terminally differentiated cells in the adult murine retina, develop and maintain their cellular identity through a combination of TFs, namely Nr1 and Nr2e3. Upon stress-induced photoreceptor toxicity, we observed decreased ATAC signal for not only Nr1 and Nr2e3, but for their respective target genes as well, including Rho and Gnat1. This corresponded to an overall decrease in downstream gene expression, as demonstrated by pseudo-scRNA-Seq, in photoreceptors one day after light damage. Taken together, our data suggest that the initial stages of stress-induced photoreceptor degeneration involve globally reduced chromatin accessibility, resulting in decreased TF binding and an altered transcriptome that drives apoptosis (FIG. 1).

Following the initial insult to photoreceptors, a delayed immune response emerges, as evidenced by increased ATAC signal in key inflammatory response genes, such as Ccl4 and Socs3. This is accompanied by widespread upregulation of gene expression, as demonstrated by pseudo-scRNA-Seq, in activated microglia 3 days after light damage. Specifically, our analysis revealed significantly increased expression of various pro-inflammatory genes including Ccl4, Ifi204, Ddx58, Cfi, C3, Nfkb2, Gfap, and Cd68 following light damage, consistent with inflammasome activation and a reactive gliosis that functions primarily to phagocytose apoptotic photoreceptor debris. Of particular interest, inflammasome activation involving chemokines such as Ccl4, as well as interferon signaling which may involve Ifi204 and Ddx58, has been described in the clinical context of AMD. Likewise, complement pathway genes Cfi and C3 have also been implicated in genome-wide association studies (GWAS) of AMD. Taken together, this evidence supports potentially conserved immune response pathways underlying photoreceptor degeneration in our mouse model and in clinical cases of AMD.

The data shown herein demonstrate that our light-sensitive mouse model of stress-induced photoreceptor degeneration recapitulates the epigenetic hallmarks of human AMD. Moreover, the potentially conserved pathways between the two species underlying the pathogenesis of photoreceptor degeneration support the use of our mouse model in subsequent studies to further address causality, whereas human studies have largely been limited to correlative analyses. Additionally, use of the novel methodology described herein as pseudo-scRNA-Seq, to ascertain cell type-specific insights from bulk RNA-Seq data cross-referenced against a generic scRNA-Seq dataset, establishes a cost-effective framework for numerous potential applications in a variety of experimental contexts. Indeed, this framework may ultimately be leveraged to extend far beyond the context of retinal degenerative disease to provide unique mechanistic insights on disease progression in any organ system of interest.

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

We claim the following:

1. A method of treating age-related macular degeneration in a subject in need thereof, the method comprising:

administering to the subject therapeutically effective amounts of agents that attenuate stress-induced chromatin remodeling associated with age-related macular degeneration, wherein the agents comprise a histone deacetylase 11 (HDAC11) inhibitor and a suppressor of variegation 3-9 homolog 2 (SUV39H2) inhibitor.

2. The method of claim 1, wherein the age-related macular degeneration is associated with an increase in HDAC11 and SUV39H2 in the subject's eye.

3. The method of claim 1, wherein the age-related macular degeneration is associated with a decrease in H3K27ac in the retina and/or an increase in H3K9me in the retinal pigment epithelium and/or choroid of the subject and the agents are administered to the subject at amounts effective to increase H3K27ac in the retina and/or decrease in H3K9me in the retinal pigment epithelium and/or choroid of the subject.

4. The method of claim 1, wherein the age-related macular degeneration manifests as at least one of the following conditions: autofluorescent spots indicative of retinal pathology detected in the fundus by Scanning Laser Ophthalmoscopy (SLO), thinning of the photoreceptor containing outer nuclear layer (ONL) as characterized by Optical Coherence Tomography (OCT), a global reduction of chromatin accessibility as determined by an Assay for Transposase-Accessible Chromatin using Sequencing (ATAC-Seq), and photoreceptor degeneration.

5. The method of claim 1, wherein the HDAC11 inhibitor is a selective inhibitor of HDAC11 and/or the SUV39H2 inhibitor is a selective inhibitor of SUV39H2.

6. The method of claim 1, wherein the HDAC11 inhibitor is selected from SIS17, Quisinostat (JNJ-26481585), Fimepinostat (CUDC-907), Pracinostat (SB939), Mocetinostat (MGCD0103, MG0103), or Domatinostat (4SC-202).

7. The method of claim 1, wherein the SUV39H2 inhibitor is selected from OTS186935 or OTS193320.

8. The method of claim 1, wherein the agents are delivered to the subject by at least one of topical administration, systemic administration, intravitreal injection, and intraocular delivery.

* * * * *